(12) United States Patent
Baran, Jr. et al.

(10) Patent No.: US 9,499,737 B2
(45) Date of Patent: Nov. 22, 2016

(54) METHOD FOR TREATING HYDROCARBON-BEARING FORMATIONS WITH FLUORINATED AMINE

(75) Inventors: Jimmie R. Baran, Jr., Prescott, WI (US);
(Continued)

(73) Assignee: 3M Innovative Properties Company, St. Paul, MN (US)

( * ) Notice: Subject to any disclaimer, the term of this patent is extended or adjusted under 35 U.S.C. 154(b) by 404 days.

(21) Appl. No.: 13/996,863

(22) PCT Filed: Dec. 21, 2011

(86) PCT No.: PCT/US2011/066367
§ 371 (c)(1),
(2), (4) Date: Jun. 21, 2013

(87) PCT Pub. No.: WO2012/088216
PCT Pub. Date: Jun. 28, 2012

(65) Prior Publication Data
US 2013/0264061 A1     Oct. 10, 2013

Related U.S. Application Data

(60) Provisional application No. 61/425,498, filed on Dec. 21, 2010.

(51) Int. Cl.
*C09K 8/60* (2006.01)
*E21B 43/16* (2006.01)
(Continued)

(52) U.S. Cl.
CPC ............ *C09K 8/602* (2013.01); *C07C 303/40* (2013.01); *C07C 311/08* (2013.01); *C09K 8/68* (2013.01); *C09K 8/88* (2013.01); *E21B 43/26* (2013.01)

(58) Field of Classification Search
CPC .................... C09K 8/584; C09K 8/602
(Continued)

(56) References Cited

U.S. PATENT DOCUMENTS 2,803,615 A   8/1957   Ahlbrecht
3,311,167 A   3/1967   O'Brien
(Continued)

FOREIGN PATENT DOCUMENTS

CA       2009732       8/1990
CN       101407716     4/2009
(Continued)

OTHER PUBLICATIONS

Adibhatla, "Effect of Surfactants on Wettability of Near-wellbore Regions of Gas Reservoirs", Journal of Petroleum Science and Engineering, 2006, vol. 52, pp. 227-236. (XP002519991).
(Continued)

*Primary Examiner* — Aiqun Li

(57) ABSTRACT

A method of modifying a surface of a hydrocarbon-bearing formation is disclosed. The method includes contacting the surface of the hydrocarbon-bearing formation with a fluorinated amine, and the surface of the hydrocarbon-bearing formation includes a carbonate. The method can typically include introducing a treatment composition comprising solvent and at least one of the fluorinated amine or a salt thereof into the carbonate hydrocarbon-bearing formation. Hydrocarbon-bearing formations treated according to the method are also disclosed. Certain fluorinated amines useful for treating carbonate hydrocarbon-bearing formations and methods of making them are also disclosed.

13 Claims, 2 Drawing Sheets

(75) Inventors: George G. I. Moore, Afton, MN (US);
Nathan E. Schultz, Lakeland, MN (US); Dean M. Moren, North St. Paul, MN (US); Yu Yang, Eden Prairie, MN (US); Rudolf J. Dams, Antwerp (BE)

(51) Int. Cl.
| | |
|---|---|
| E21B 43/26 | (2006.01) |
| C07C 303/40 | (2006.01) |
| C07C 311/08 | (2006.01) |
| C09K 8/68 | (2006.01) |
| C09K 8/88 | (2006.01) |

(58) Field of Classification Search
USPC .............. 507/205; 166/305.1, 308.2, 242.1
See application file for complete search history.

(56) References Cited

U.S. PATENT DOCUMENTS

| | | | |
|---|---|---|---|
| 3,394,758 A | 7/1968 | Terry | |
| 3,458,571 A * | 7/1969 | Tokoli | 564/96 |
| 3,555,100 A | 1/1971 | Garth | |
| 3,653,442 A | 4/1972 | Ross | |
| 3,787,351 A | 1/1974 | Olson | |
| 3,902,557 A | 9/1975 | Shaughnessy | |
| 4,018,689 A | 4/1977 | Thompson | |
| 4,147,851 A | 4/1979 | Raynolds | |
| 4,200,154 A | 4/1980 | Tate | |
| 4,329,236 A | 5/1982 | Alford | |
| 4,432,882 A | 2/1984 | Raynolds | |
| 4,440,653 A | 4/1984 | Briscoe | |
| 4,460,791 A | 7/1984 | Cooke | |
| 4,557,837 A | 12/1985 | Clark, III | |
| 4,565,639 A | 1/1986 | Penny | |
| 4,585,065 A | 4/1986 | Penny | |
| 4,594,177 A | 6/1986 | Lantz et al. | |
| 4,594,200 A | 6/1986 | Penny | |
| 4,609,477 A | 9/1986 | Crema | |
| 4,702,849 A | 10/1987 | Penny | |
| 4,753,740 A | 6/1988 | Marlett | |
| 4,767,545 A | 8/1988 | Karydas | |
| 4,817,715 A | 4/1989 | Peru | |
| 4,823,873 A | 4/1989 | Karydas | |
| 4,921,619 A | 5/1990 | Karydas | |
| 4,923,009 A | 5/1990 | Watkins | |
| 4,993,448 A | 2/1991 | Karydas | |
| 4,997,580 A | 3/1991 | Karydas | |
| 5,042,580 A | 8/1991 | Cullick | |
| 5,069,283 A * | 12/1991 | Mack | 166/308.6 |
| 5,085,786 A | 2/1992 | Alm | |
| 5,092,405 A | 3/1992 | Prukop | |
| 5,129,457 A | 7/1992 | Sydansk | |
| 5,186,257 A | 2/1993 | Stahl | |
| 5,247,993 A | 9/1993 | Sarem | |
| 5,310,002 A | 5/1994 | Blauch | |
| 5,358,052 A | 10/1994 | Gidley | |
| 5,514,301 A | 5/1996 | Bil | |
| 5,980,642 A * | 11/1999 | Strepparola | C08G 65/007 134/2 |
| 6,127,485 A | 10/2000 | Klun | |
| 6,165,948 A | 12/2000 | Dewenter | |
| 6,182,759 B1 | 2/2001 | Burger | |
| 6,206,102 B1 | 3/2001 | Pusch | |
| 6,225,263 B1 | 5/2001 | Collins | |
| 6,579,572 B2 | 6/2003 | Espin | |
| 6,660,693 B2 | 12/2003 | Miller | |
| 6,664,354 B2 | 12/2003 | Savu | |
| 6,689,854 B2 | 2/2004 | Fan | |
| 6,729,409 B1 | 5/2004 | Gupta | |
| 6,911,417 B2 | 6/2005 | Chan | |
| 6,945,327 B2 | 9/2005 | Ely | |
| 6,972,274 B1 | 12/2005 | Slikta | |
| 7,084,094 B2 | 8/2006 | Gunn | |
| 7,101,492 B2 | 9/2006 | Parent | |
| 7,164,041 B1 | 1/2007 | Moore | |
| 7,165,613 B2 | 1/2007 | Chan | |
| 7,294,610 B2 | 11/2007 | Savu | |
| 7,417,099 B2 | 8/2008 | Savu | |
| 7,585,817 B2 | 9/2009 | Pope | |
| 7,629,298 B2 | 12/2009 | Arco | |
| 7,772,162 B2 | 8/2010 | Pope | |
| 7,811,978 B2 | 10/2010 | Savu | |
| 7,855,169 B2 | 12/2010 | Pope | |
| 7,985,723 B2 | 7/2011 | Savu | |
| 8,043,998 B2 | 10/2011 | Pope | |
| 8,138,127 B2 | 3/2012 | Pope | |
| 8,176,981 B2 | 5/2012 | Savu | |
| 8,236,737 B2 | 8/2012 | Fan | |
| 8,261,825 B2 | 9/2012 | Pope | |
| 8,403,050 B2 | 3/2013 | Pope | |
| 8,418,759 B2 | 4/2013 | Moore | |
| 8,476,385 B2 | 7/2013 | Dams | |
| 8,629,089 B2 | 1/2014 | Dams | |
| 8,678,090 B2 | 3/2014 | Baran, Jr. | |
| 9,057,012 B2 | 6/2015 | Dams | |
| 2003/0092581 A1 | 5/2003 | Crews | |
| 2005/0244641 A1 | 11/2005 | Vincent | |
| 2006/0045979 A1 | 3/2006 | Dams | |
| 2006/0264334 A1 | 11/2006 | Gupta | |
| 2007/0015669 A1 | 1/2007 | Zhang | |
| 2007/0015864 A1 | 1/2007 | Hintzer | |
| 2007/0029085 A1 | 2/2007 | Panga | |
| 2009/0253595 A1 | 10/2009 | Qu | |
| 2009/0281002 A1 | 11/2009 | Casper | |
| 2010/0152071 A1 | 6/2010 | Pope | |
| 2010/0181068 A1 | 7/2010 | Pope | |
| 2010/0224361 A1 | 9/2010 | Pope | |
| 2010/0270019 A1 | 10/2010 | Pope | |
| 2010/0276142 A1 | 11/2010 | Skildum | |
| 2011/0056689 A1 | 3/2011 | Baran, Jr. | |
| 2011/0124532 A1 | 5/2011 | Maurer | |
| 2011/0136704 A1 | 6/2011 | Sharma | |
| 2011/0177983 A1 | 7/2011 | Baran, Jr. | |
| 2011/0201531 A1 | 8/2011 | Sharma | |
| 2012/0071372 A1 | 3/2012 | Iaconelli | |
| 2012/0097393 A1 | 4/2012 | Dams | |
| 2013/0269932 A1 | 10/2013 | Dams | |
| 2014/0014330 A1 | 1/2014 | Dams | |

FOREIGN PATENT DOCUMENTS

| | | |
|---|---|---|
| EP | 1311637 | 5/2003 |
| GB | 2031482 | 4/1980 |
| RU | 1706204 | 11/1994 |
| WO | WO 03-089540 | 10/2003 |
| WO | WO 2005-028589 | 3/2005 |
| WO | WO 2005-035936 | 4/2005 |
| WO | WO 2007-017806 | 2/2007 |
| WO | WO 2007-033489 | 3/2007 |
| WO | WO 2007-097975 | 8/2007 |
| WO | WO 2009-085899 | 7/2009 |
| WO | WO 2009-148831 | 12/2009 |
| WO | WO 2010-132333 | 11/2010 |
| WO | WO 2010/132362 | 11/2010 |
| WO | WO 2010/144352 | 12/2010 |
| WO | WO 2010/144398 | 12/2010 |
| WO | WO 2011/005666 | 1/2011 |

OTHER PUBLICATIONS

Al-Anazi, "A Successful Methanol Treatment in a Gas-Condensate Reservoir: Field Application", Mar. 2003, Society of Petroleum Engineers Inc., pp. 1-9, SPE 80901.

Clark, "Use of Fluorochemical Surfactants in Nonaqueous Stimulation Fluids," Oct. 1980, Journal of Petroleum Chemistry, vol. 32, No. 10, pp. 1695-1697.

Crema, "Foaming of Anhydrous Methanol for Well Stimulation", Apr. 1985, Society of Petroleum Engineers Inc., 4 pages, SPE 13565.

Fahes, "Wettability Alteration to Intermediate Gas-Wetting in Gas-Condensate Reservoirs at High Temperatures", Oct. 9-12, 2005, SPE Annual Technical Conference and Exhibition, Dallas, TX, pp. 1-14. SPE 96184.

(56) References Cited

OTHER PUBLICATIONS

Kumar, "Improving the Gas and Condensate Relative Permeability Using Chemical Treatments", May 15-17, 2006, SPE Gas Technology Symposium, Calgary, Alberta, pp. 1-9. SPE 100529.
Li, "Experimental Study of Wettability Alteration to Preferential Gas-Wetting in Porous Media and Its Effects", SPE Reservoir Evaluation & Engineering, Apr. 2000, vol. 3, No. 2, pp. 139-149.
McLeod, "The Use of Alcohol in Gas Well Stimulation", Nov. 10-11, 1966, SPE Eastern Regional Meeting, Columbus, Ohio, pp. 1-13, SPE 1663.
Noh, "Effect of Wettability on High-Velocity Coefficient in Two-Phase Gas-Liquid Flow", SPE Annual Technical Conference and Exhibition held in San Antonio, TX, Sep. 24-27, 2006, pp. 1-8, SPE 102773.
Noh, "Experimental Study of Wettability Alteration for Reservoir Rock", Project 3-Gas Condensate Reservoirs Part 2, Reservoir Engineering Research Institute, Apr. 1-Jun. 30, 2005, pp. 1-7.
Panga, "Preventive Treatment for Enhancing Water Removal from Gas Reservoirs by Wettability Alteration", Mar. 11-14, 2007, 15th SPE Middle East Oil & Gas Show and Conference, Kingdom of Bahrain, pp. 1-12. SPE 105367.
Tang, "Relative Permeability Modification in Gas/Liquid Systems Through Wettability Alteration to Intermediate Gas Wetting", SPE Reservoir Evaluation and Engineering, Dec. 2002, vol. 5, No. 6, pp. 427-436. SPE 81195.
International Search Report for PCT International Application No. PCT/US2011/066367, mailed on Oct. 30, 2012, 7 pages.
Supplementary European Search Report for Application No. EP 11 85 1239, Dec. 1, 2014, 3 pages.

\* cited by examiner

METHOD FOR TREATING HYDROCARBON-BEARING FORMATIONS WITH FLUORINATED AMINE

CROSS REFERENCE TO RELATED APPLICATION

This application is a national stage filing under 35 U.S.C. 371 of PCT/US2011/066367, filed Dec. 21, 2011, which claims priority to U.S. Provisional Application No. 61/425,498, filed on Dec. 21, 2010, the disclosure of which is incorporated by reference herein in its entirety.

BACKGROUND

In the oil and gas industry, certain surfactants (including certain fluorinated surfactants) are known as fluid additives for various downhole operations (e.g., fracturing, water-flooding, and drilling). Often, these surfactants function to decrease the surface tension of the fluid or to stabilize foamed fluids.

Some hydrocarbon and fluorochemical compounds have been used to modify the wettability of reservoir rock, which may be useful, for example, to prevent or remedy water blocking (e.g., in oil or gas wells) or liquid hydrocarbon accumulation (e.g., in gas wells) in the vicinity of the well bore (i.e., the near well bore region). Water blocking and liquid hydrocarbon accumulation may result from natural phenomena (e.g., water-bearing geological zones or condensate banking) and/or operations conducted on the well (e.g., using aqueous or hydrocarbon fluids). Water blocking and condensate banking in the near well bore region of a hydrocarbon-bearing geological formation can inhibit or stop production of hydrocarbons from the well and hence are typically not desirable. Not all hydrocarbon and fluorochemical compounds, however, provide the desired wettability modification. And some of these compounds modify the wettability of siliciclastic hydrocarbon-bearing formations but not carbonate formations.

SUMMARY

The method of treating a hydrocarbon-bearing formation with a fluorinated amine disclosed herein may be useful, for example, for increasing the permeability in carbonate hydrocarbon-bearing formations wherein two phases (i.e., a gas phase and an oil phase) of the hydrocarbons are present, (e.g., in gas wells having retrograde condensate and oil wells having black oil or volatile oil). The method is also typically useful for increasing the permeability in hydrocarbon-bearing formations having brine (e.g., connate brine and/or water blocking). Treatment of a near wellbore region of an oil and/or gas well that has at least one of brine or two phases of hydrocarbons in the near wellbore region may increase the productivity of the well. Unexpectedly, the neutral fluorinated amines described herein have been found to modify carbonate formations even though they are not negatively charged.

Although not wishing to be bound by theory, it is believed that the fluorinated amines disclosed herein generally adsorb to the surface of a carbonate hydrocarbon-bearing formation under downhole conditions and modify the wetting properties of the rock in the formation to facilitate the removal of hydrocarbons and/or brine. The fluorinated amine may remain on the rock for the duration of an extraction of hydrocarbons from the formation (e.g., 1 week, 2 weeks, 1 month, or longer).

In one aspect, the present disclosure provides a method of modifying a surface of a hydrocarbon-bearing formation, the method comprising contacting the surface of the hydrocarbon-bearing formation with a fluorinated amine, wherein the surface of the hydrocarbon-bearing formation comprises a carbonate. In some embodiments, contacting the surface of the hydrocarbon-bearing formation comprises introducing a treatment composition comprising solvent and at least one of the fluorinated amine or a salt thereof into the hydrocarbon-bearing formation.

In another aspect, the present disclosure provides a hydrocarbon-bearing formation comprising a carbonate treated according to the method disclosed herein.

Hydrocarbon-bearing formations that comprise carbonate include limestone or dolomite formations, wherein limestone or dolomite forms at least a portion (e.g., at least 50, 60, 75, or 90 percent by weight) of the formation. In some embodiments of the foregoing aspects, the hydrocarbon-bearing formation comprises limestone (e.g., at least 50, 60, 75, or 90 percent by weight limestone).

In some embodiments of the foregoing aspects, the hydrocarbon-bearing formation is penetrated by a wellbore, wherein a region near the wellbore is treated with the fluorinated amine. The region near the wellbore (i.e., near wellbore region) includes a region within about 25 feet (in some embodiments, 20, 15, or 10 feet) of the wellbore. In some of these embodiments, the method further comprises obtaining (e.g., pumping or producing) hydrocarbons from the well bore after treating the hydrocarbon-bearing formation with the fluorinated amine.

In another aspect, the present disclosure provides a method of making a fluorinated amine, the method comprising:

combining a fluoroalkyl compound having an acidic hydrogen and cyclic imidate represented by formula

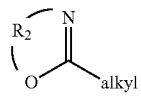

to provide a fluorinated amide; and hydroylzing the fluorinated amide to provide the fluorinated amine, wherein $R^2$ is a straight chain or branched alkylene having up to 10 carbon atoms, and wherein the $R^2$ group together with the —O—C(=N)— group form a five- or six-membered ring.

In another aspect, the present disclosure provides a compound represented by formula Rf—SO$_2$N(—R$^2$—NH$_2$)$_2$ or a salt thereof, wherein Rf is fluoroalkyl having up to 10 carbon atoms; and each $R^2$ is independently a straight chain or branched alkylene having 2 or 3 in-chain carbon atoms and up to 10 carbon atoms total. The compound may be useful, for example, as a fluorinated amine in the method of modifying the surface of a hydrocarbon-bearing formation disclosed herein.

In this application:

Terms such as "a", "an" and "the" are not intended to refer to only a singular entity, but include the general class of which a specific example may be used for illustration. The terms "a", "an", and "the" are used interchangeably with the term "at least one".

The phrases "comprises at least one of" and "at least one of" followed by a list refers to any one of the items in the list and any combination of two or more items in the list.

The term "brine" refers to water having at least one dissolved electrolyte salt therein (e.g., sodium chloride, calcium chloride, strontium chloride, magnesium chloride, potassium chloride, ferric chloride, ferrous chloride, and hydrates thereof) at any nonzero concentration (in some embodiments, less than 1000 parts per million by weight (ppm), or greater than 1000 ppm, greater than 10,000 ppm, greater than 20,000 ppm, 30,000 ppm, 40,000 ppm, 50,000 ppm, 100,000 ppm, 150,000 ppm, or even greater than 200,000 ppm).

The term "hydrocarbon-bearing formation" includes both hydrocarbon-bearing formations in the field (i.e., subterranean hydrocarbon-bearing formations) and portions of such hydrocarbon-bearing formations (e.g., core samples).

The term "contacting" includes placing the fluorinated amine within a hydrocarbon-bearing formation using any suitable manner known in the art (e.g., pumping, injecting, pouring, releasing, displacing, spotting, or circulating the fluorinated amine into a well, well bore, or hydrocarbon-bearing formation.

The term "solvent" refers to a homogeneous liquid material, which may be a single compound or a combination of compounds and which may or may not include water, that is capable of at least partially dissolving the fluorinated amine disclosed herein at 25° C.

"Alkyl group" and the prefix "alk-" are inclusive of both straight chain and branched chain groups and of cyclic groups. Unless otherwise specified, alkyl groups herein have up to 20 carbon atoms. Cyclic groups can be monocyclic or polycyclic and, in some embodiments, have from 3 to 10 ring carbon atoms. "Alkylene" is the divalent or multivalent form of "alkyl".

The term "aryl" as used herein includes carbocyclic aromatic rings or ring systems, for example, having 1, 2, or 3 rings, optionally containing at least one heteroatom (e.g., O, S, or N) in the ring, and optionally substituted by up to five substituents including one or more alkyl groups having up to 4 carbon atoms (e.g., methyl or ethyl), alkoxy having up to 4 carbon atoms, halo (i.e., fluoro, chloro, bromo or iodo), hydroxy, or nitro groups. Examples of aryl groups include phenyl, naphthyl, biphenyl, fluorenyl as well as furyl, thienyl, oxazolyl, and thiazolyl. "Arylene" is the divalent form of "aryl".

"Alkylarylene" refers to an "arylene" moiety to which an alkyl group is attached.

"Arylalkylene" refers to an "alkylene" moiety to which an aryl group is attached.

The term "polymer" refers to a molecule having a structure which essentially includes the multiple repetition of units derived from molecules of low relative molecular mass. The term "polymer" encompasses oligomers. The term non-polymeric refers to a molecule having a structure which does not include the multiple repetition of units derived from molecules of low relative molecular mass. Non-polymeric compounds may also be referred to as "small molecules".

The term "salt" refers to ionic compounds that are composed of cations and anions so that the product is electrically neutral. Zwitterions contain an anionic center and a cationic center in the same molecule but are not considered by one of ordinary skill in the art to be salts.

The term "fluoroalkyl group" includes linear, branched, and/or cyclic alkyl groups in which all C—H bonds are replaced by C—F bonds as well as groups in which hydrogen or chlorine atoms are present instead of fluorine atoms. In some embodiments, up to one atom of either hydrogen or chlorine is present for every two carbon atoms. In some embodiments of fluoroalkyl groups, when at least one hydrogen or chlorine is present, the fluoroalkyl group includes at least one trifluoromethyl group. The term "perfluoroalkyl group" includes linear, branched, and/or cyclic alkyl groups in which all C—H bonds are replaced by C—F bonds. The term "interrupted by up to 5 ether groups" refers to having fluoroalkyl on both sides of the ether group.

The term "productivity" as applied to a well refers to the capacity of a well to produce hydrocarbons (i.e., the ratio of the hydrocarbon flow rate to the pressure drop, where the pressure drop is the difference between the average reservoir pressure and the flowing bottom hole well pressure (i.e., flow per unit of driving force)).

All numerical ranges are inclusive of their endpoints and non-integral values between the endpoints unless otherwise stated.

BRIEF DESCRIPTION OF THE DRAWINGS

For a more complete understanding of the features and advantages of the present disclosure, reference is now made to the detailed description along with the accompanying figures and in which.

DETAILED DESCRIPTION

Figure 1:
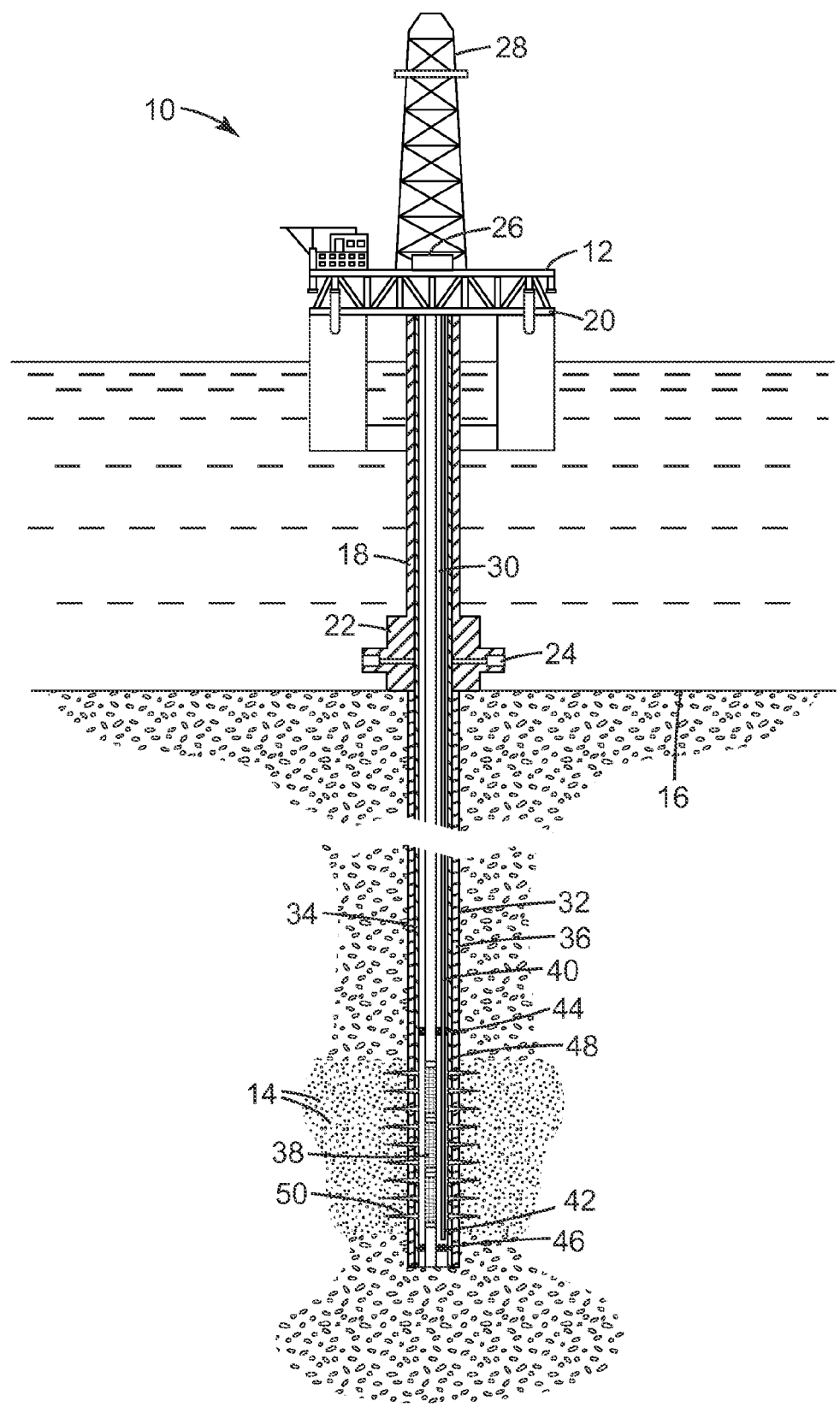
FIG. 1 is a schematic illustration of an exemplary embodiment of an offshore oil platform operating an apparatus for progressively treating a near wellbore region according to some embodiments of the present disclosure.

The method according to the present disclosure includes contacting a hydrocarbon-bearing formation with a fluorinated amine. The amine may be a primary, secondary, or tertiary amine and may have one amine functional group or two or more amine functional groups. It will be understood by a person having ordinary skill in the art that an amine is a neutral organic compound bearing an —$NR_2$ group. The R groups may be the same or different and may include hydrogen, alkyl or alkylene groups, aryl or arylene groups, etc. The nitrogen atom is understood to be neutral and to have a lone pair of electrons, features that distinguish them from quaternary ammonium compounds, which have a permanent positive charge regardless of pH.

Fluorinated amines may optionally be delivered to the hydrocarbon-bearing formation in salt form. In these embodiments, without wanting to be bound by theory, it is believed that the free amine is liberated when it comes in contact with the hydrocarbon-bearing formation. Useful salts of fluorinated amines include halide salts (i.e., hydrofluoride, hydrochloride, hydrobromide, and hydroiodide), organic acid salts (e.g., hydroacetate and hydrocitrate), organic sulfonic acid salts (e.g., hydroalkanesulfonates), hydronitrate, hydrotetrafluoroborate, and numerous others. The anions or organic acid salts and sulfonic acid salts may be partially fluorinated or perfluorinated.

In some embodiments, the fluorinated amine does not have polymeric repeating units comprising amine groups. In some of these embodiments, the fluorinated amine is non-polymeric. In other of these embodiments, the fluorinated amine may comprise fluorinated repeating units (e.g., in a polyfluoropolyether).

In some embodiments, the fluorinated amine is represented by formula Rf-Q-X—$NR_2$. In some of these embodiments, Rf may be a fluoroalkyl group having up to 10 carbon atoms (e.g., up to 8, 6, or 4 carbon atoms, for example, in a range from 2 to 10, 4 to 8, or 2 to 6 carbon atoms). Exemplary Rf groups include trifluoromethyl, perfluoroethyl, 1,1,2,2-tetrafluoroethyl, 2-chlorotetrafluoroethyl, perfluoro-n-propyl, perfluoroisopropyl, perfluoro-n-butyl, 1,1,2,3,3,3-hexafluoropropyl, perfluoroisobutyl, perfluoro-sec-butyl, or perfluoro-tert-butyl, perfluoro-n-pentyl, pefluoroisopentyl, perfluorohexyl, perfluoroheptyl, or perfluorooctyl. In some embodiments, Rf is perfluorobutyl (e.g., perfluoro-n-butyl, perfluoroisobutyl, or perfluoro-sec-butyl). In some embodiments, Rf is perfluoropropyl (e.g., perfluoro-n-propyl). Rf may be a mixture of fluoroalkyl groups.

In some embodiments, Rf is a polyfluoropolyether group. The term "polyfluoropolyether" refers to a compound or group having at least 3 (in some embodiments, at least 4, 5, 6, 7, 8, 9, 10, 11, 12, 13, 14, 15, 16, 17, 18, 19, or even 20) carbon atoms and at least 3 (in some embodiments, at least 4, 5, 6, 7, or even 8) ether linkages, wherein the hydrogen atoms on the carbon atoms are replaced with fluorine atoms. In some embodiments, Rf has up to 100, 110, 120, 130, 140, 150, or even 160 carbon atoms and up to 25, 30, 35, 40, 45, 50, 55, or even 60 ether linkages.

The polyfluoropolyether group Rf can be linear, branched, cyclic, or combinations thereof and can be saturated or unsaturated. Polyfluoropolyether groups include those in which hydrogen or chlorine atoms are present instead of fluorine atoms provided that up to one atom of either hydrogen or chlorine is present for every two carbon atoms. In some embodiments, the polyfluoropolyether group is a perfluoropolyether group (i.e., all of the hydrogen atoms on the carbon atoms are replaced with fluorine atoms). Exemplary perfluoropolyethers include perfluorinated repeating units represented by at least one of $-(C_dF_{2d})-$, $-(C_dF_{2d}O)-$, $-(CF(L'))-$, $-(CF(L')O)-$, $-(CF(L')C_dF_{2d}O)-$, $-(C_dF_{2d}CF(L')O)-$, or $(CF_2CF(L')O)-$. In these repeating units, d is typically an integer of 1 to 10. In some embodiments, d is an integer of 1 to 8, 1 to 6, 1 to 4, or 1 to 3. The L' group can be a perfluoroalkyl group optionally interrupted by at least one ether linkage or a perfluoroalkoxy group, each of which may be linear, branched, cyclic, or a combination thereof. The L' group typically has up to 12 (in some embodiments, up to 10, 8, 6, 4, 3, 2, or 1) carbon atoms. In some embodiments, the L' group can have up to 4 (in some embodiments, up to 3, 2, or 1) oxygen atoms; in some embodiments L' has no oxygen atoms. In these perfluoropolyether structures, different repeating units can be combined in a block or random arrangement to form the Rf group. Rf may be a mixture of polyfluoropolyether groups.

In some embodiments, Rf is represented by formula $R_f^a-O-(R_f^b-O-)_{z'}(R_f^c)-$, wherein $R_f^a$ is a perfluoroalkyl having 1 to 10 (in some embodiments, 1 to 6, 1 to 4, 2 to 4, or 3) carbon atoms; each $R_f^b$ is independently a perfluoroalkylene having 1 to 4 (i.e., 1, 2, 3, or 4) carbon atoms; $R_f^c$ is a perfluoroalkylene having 1 to 6 (in some embodiments, 1 to 4 or 2 to 4) carbon atoms; and z' is in a range from 2 to 50 (in some embodiments, 2 to 25, 2 to 20, 3 to 20, 3 to 15, 5 to 15, 6 to 10, or 6 to 8). Representative $R_f^a$ groups include $CF_3-$, $CF_3CF_2-$, $CF_3CF_2CF_2-$, $CF_3CF(CF_3)-$, $CF_3CF(CF_3)CF_2-$, $CF_3CF_2CF_2CF_2-$, $CF_3CF_2CF(CF_3)-$, $CF_3CF_2CF(CF_3)CF_2-$, and $CF_3CF(CF_3)CF_2CF_2-$. In some embodiments, $R_f^a$ is $CF_3CF_2CF_2-$. Representative $R_f^b$ groups include $-CF_2-$, $-CF(CF_3)-$, $-CF_2CF_2-$, $-CF(CF_3)CF_2-$, $-CF_2CF_2CF_2-$, $-CF(CF_3)CF_2-$, $-CF_2CF_2CF_2CF_2-$, and $-CF_2C(CF_3)_2-$. Representative $R_f^c$ groups include $-CF_2-$, $-CF(CF_3)-$, $-CF_2CF_2-$, $-CF_2CF_2CF_2-$, and $-CF(CF_3)CF_2-$. In some embodiments, $R_f^c$ is $-CF(CF_3)-$.

In some embodiments, $(R_f^b-O-)_{z'}$ is represented by $-[CF_2O]_i[CF_2CF_2O]_j-$, $-[CF_2O]_i[CF(CF_3)CF_2O]_j-$, $-[CF_2O]_i[CF_2CF_2CF_2O]_j-$, $-[CF_2CF_2O]_i[CF_2O]_j-$, $-[CF_2CF_2O]_i[CF(CF_3)CF_2O]_j-$, $-[CF_2CF_2O]_i[CF_2CF_2CF_2O]_j-$, $-[CF_2CF_2CF_2O]_i[CF_2CF(CF_3)O]_j-$, and $[CF_2CF_2CF_2O]_i[CF(CF_3)CF_2O]_j-$, wherein i+j is an integer of at least 3 (in some embodiments, at least 4, 5, or 6).

In some embodiments, Rf is selected from the group consisting of $C_3F_7O(CF(CF_3)CF_2O)_xCF(CF_3)-$, $C_3F_7O(CF_2CF_2CF_2O)_xCF_2CF_2-$, or $CF_3O(C_2F_4O)_yCF_2-$, wherein x has an average value in a range from 3 to 50 (in some embodiments, 3 to 25, 3 to 15, 3 to 10, 4 to 10, or 4 to 7), and wherein y has an average value in a range from 6 to 50 (in some embodiments, 6 to 25, 6 to 15, 6 to 10, 7 to 10, or 8 to 10). In some of these embodiments, Rf is $C_3F_7O(CF(CF_3)CF_2O)_xCF(CF_3)-$, wherein x has an average value in a range from 4 to 7. In some embodiments, Rf is selected from the group consisting of $CF_3O(CF_2O)_{x'}(C_2F_4O)_{y'}CF_2-$ and $F(CF_2)_3-O-(C_4F_8O)_{z''}(CF_2)_3-$, wherein x', y', and z'' each independently has an average value in a range from 3 to 50 (in some embodiments, 3 to 25, 3 to 15, 3 to 10, or even 4 to 10).

In some embodiments where Rf is a polyfluoropolyether group, including in any of the above embodiments describing polyfluoropolyether groups, Rf has a weight average molecular weight of at least 750 (in some embodiments at least 850 or even 1000) grams per mole. In some embodiments, Rf has a weight average molecular weight of up to 6000 (in some embodiments, 5000 or even 4000) grams per mole. In some embodiments, Rf has a weight average molecular weight in a range from 750 grams per mole to 5000 grams per mole. Weight average molecular weights can be measured, for example, by gel permeation chromatography (i.e., size exclusion chromatography) using techniques known in the art.

In other embodiments where Rf is a polyfluoropolyether group, Rf is $CF_3-(O-CF_2)_z-$ or $CF_3-O-(CF_2)_3-O-CF_2-$, wherein z is a number from 2 to 7 (e.g., 2, 3, 4, 5, 6, or 7). In some embodiments, z is an integer from 2 to 6, 2 to 5, 2 to 4, or 3 to 4.

In some embodiments, Rf is a partially fluorinated polyfluoropolyether group selected from the group consisting of $Rf^d-(O)_r-CHF-(CF_2)_n-$, $[Rf^e-(O)_t-C(L)H-CF_2-O]_{m'}-W'-$, and $CF_3CFH-O-(CF_2)_{p'}-$. $Rf^d$ and $Rf^e$ independently represent a partially or fully fluorinated alkyl group having from 1 to 10 carbon atoms and optionally interrupted with at least one oxygen atom. L is selected from the group consisting of F and $CF_3$. In some embodiments, L is F. In other embodiments, L is $CF_3$. W' is selected from the group consisting of alkylene and arylene. Alkylene includes linear, branched, and cyclic alkylene groups having from 1 to 10 (in some embodiments, 1 to 4) carbon atoms. In some embodiments, W' is methylene. In some embodiments, W' is ethylene. Arylene includes groups having 1 or 2 aromatic rings, optionally having at least one heteroatom (e.g., N, O, and S) in the ring, and optionally substituted with at least one alkyl group or halogen atom. In some embodiments, W' is phenylene. In the partially fluorinated polyfluoropolyethers, r is 0 or 1, with the proviso that when r is 0, then $Rf^d$ is interrupted with at least one oxygen atom, and t is 0 or 1. In embodiments wherein t is 0, $Rf^e$ is typically interrupted by at least one oxygen atom.

In the formulas where m, n, or p is present, m' is 1, 2, or 3 (in some embodiments, 1); n is 0 or 1; and p' is a number from 1 to 6. In some of these embodiments, Rf has a weight average molecular weight of up to 600 grams per mole (in some embodiments, up to 500, 400, or even up to 300 grams per mole).

In some embodiments of the partially fluorinated polyfluoropolyether groups described above, $Rf^d$ and $Rf^e$ include linear and branched alkyl groups. In some embodiments, $Rf^d$ and/or $Rf^e$ is linear. In some embodiments, $Rf^d$ and $Rf^e$ independently represent a fully fluorinated alkyl group having up to 6 (in some embodiments, 5, 4, 3, 2, or 1) carbon atoms. In some embodiments, $Rf^d$ and $Rf^e$ independently represent a fully fluorinated alkyl group interrupted with at least one oxygen atom, of which the alkyl groups between oxygen atoms have up to 6 (in some embodiments, 5, 4, 3, 2, or 1) carbon atoms, and wherein the terminal alkyl group has up to 6 (in some embodiments, 5, 4, 3, 2, or 1) carbon atoms. In some embodiments, $Rf^d$ and $Rf^e$ independently represent a partially fluorinated alkyl group having up to 6 (in some embodiments, 5, 4, 3, 2, or 1) carbon atoms and up to 2 hydrogen atoms. In some embodiments, $Rf^d$ and $Rf^e$ independently represent a partially fluorinated alkyl group having up 2 hydrogen atoms interrupted with at least one oxygen atom, of which the alkyl groups between oxygen atoms have up to 6 (in some embodiments, 5, 4, 3, 2, or 1) carbon atoms, and wherein the terminal alkyl group has up to 6 (in some embodiments, 5, 4, 3, 2, or 1) carbon atoms.

In some embodiments, Rf, $Rf^d$ and $Rf^e$ are independently represented by formula $R_f^1$—$[OR_f^2]_a$—$[OR_f^3]_b$—. $R_f^1$ is a perfluorinated alkyl group having from 1 to 6 (in some embodiments, 1 to 4) carbon atoms. $R_f^2$ and $R_f^3$ are each independently perfluorinated alkylene having from 1 to 4 carbon atoms. "a" and b are each independently a number having a value from 0 to 4, and the sum of "a" and b is at least 1. In some of these embodiments, t is 1, and r is 1.

In some embodiments, Rf, $Rf^d$ and $Rf^e$ are independently represented by formula $R_f^4$—$[OR_f^5]_{a'}$—$[OR_f^6]_{b'}$—O—$CF_2$—. $R_f^4$ is a perfluorinated alkyl group having from 1 to 6 (in some embodiments, 1 to 4) carbon atoms. $R_f^5$ and $R_f^6$ are each independently perfluorinated alkylene having from 1 to 4 carbon atoms. a' and b' are each independently numbers having a value from 0 to 4. In some of these embodiments, t is 0, and r is 0.

In some embodiments, Rf, $Rf^d$ and $Rf^e$ are independently represented by formula $R_f^7$—$(OCF_2)_{p'}$—, wherein p' is a number from 1 to 6 (in some embodiments, 1 to 4), and $R_f^7$ is selected from the group consisting of a partially fluorinated alkyl group having 1, 2, 3, 4, 5, or 6 carbon atoms and 1 or 2 hydrogen atoms and a fully fluorinated alkyl group having 1, 2, 3 or 4 carbon atoms.

In some embodiments, Rf, $Rf^d$ and $Rf^e$ are independently represented by formula $R_f^8$—O—$(CF_2)_{p'}$—, wherein p' is a number from 1 to 6 (in some embodiments, 1 to 4) and $R_f^8$ is selected from the group consisting of a partially fluorinated alkyl group having 1, 2, 3, 4, 5, or 6 carbon atoms and 1 or 2 hydrogen atoms and a fully fluorinated alkyl group having 1, 2, 3 or 4 carbon atoms.

In some embodiments, fluorinated amines disclosed herein have an Rf group represented by $CF_3CFH$—O—$(CF_2)_{p'}$. In some of these embodiments, Rf is selected from the group consisting of $CF_3CFH$—O—$(CF_2)_3$— and $CF_3CFH$—O—$(CF_2)_5$—. In other embodiments, fluorinated amines disclosed herein have an Rf group represented by $CF_3$—$(O$—$CF_2)_z$—. In some of these embodiments, z is a number from 2 to 6, 2 to 5, 2 to 4, 3 to 5, or 3 to 4. In yet other embodiments, fluorinated amines disclosed herein have an Rf represented by $CF_3$—O—$(CF_2)_3$—O—$CF_2$—.

Other useful Rf structures include partially fluorinated Rf groups disclosed, for example, in PCT International Pub. No. WO 2008/154345 A1 (Dams et al.), pages 8 to 10, the disclosure of which is incorporated herein by reference.

In the compound represented by formula Rf-Q-X—$NR_2$, Q is a bond, —$SO_2N(R')$—, or —$C(O)N(R')$—. When Q is a bond, it will be understood that Q is absent, and the compound represented by formula Rf-Q-X—$NR_2$ may also be represented by formula Rf—X—$NR_2$. In some embodiments, Q is —$SO_2N(R')$—. In some embodiments, Q is —$C(O)N(R')$—. In any of these embodiments, R' is hydrogen, alkyl having up to 4 carbon atoms (e.g., methyl, ethyl, n-propyl, isopropyl, n-butyl, or isobutyl), or —X—$NR_2$. In some embodiments, R' is hydrogen. In some embodiments, R' is methyl or ethyl. In some embodiments, R' is —X—$NR_2$, with X and R having any of the definitions described below.

In the compound represented by formula Rf-Q-X—$NR_2$, X is alkylene, arylene, alkylarylene, or arylalkylene, wherein alkylene, arylene, alkylarylene, and arylalkylene are each optionally interrupted with at least one of —O—, —C(O)—, —$S(O)_{0-2}$—, —N(R')—, —$SO_2N(R')$—, —C(O)N(R')—, —C(O)—O—, —O—C(O)—, —OC(O)—N(R')—, —N(R')—C(O)—O—, or —N(R')—C(O)—N(R')—, wherein R' is hydrogen, alkyl having up to 4 carbon atoms (e.g., methyl, ethyl, n-propyl, isopropyl, n-butyl, or isobutyl), or —X—$NR_2$. In some of these embodiments, R' is hydrogen. In some of these embodiments, R' is methyl or ethyl. The phrase "interrupted with at least one of —O—, —C(O)—, —$S(O)_{0-2}$—, —N(R')—, —$SO_2N(R')$—, —C(O)N(R')—, —C(O)—O—, —O—C(O)—, —OC(O)—N(R')—, —N(R')—C(O)—O—, or —N(R')—C(O)—N(R')—" refers to having a portion of the alkylene, arylene, alkylarylene, and arylalkylene on either side of the —O—, —C(O)—, —$S(O)_{0-2}$—, —N(R')—, —$SO_2N(R')$—, —C(O)N(R')—, —C(O)—O—, —O—C(O)—, —OC(O)—N(R')—, —N(R')—C(O)—O—, or —N(R')—C(O)—N(R')—. An exemplary alkylene that is interrupted with —O— is —$CH_2$—$CH_2$—O—$CH_2$—$CH_2$—. In some embodiments, X is alkylene, which may have, in some embodiments, up to 4, 3, or 2 carbon atoms. In some embodiments, X is —$CH_2$—$CH_2$—. In embodiments, where R' is —X—$NR_2$, each X may be independently selected. In some of these embodiments, each X is independently alkylene (in some embodiments, having up to 4, 3, or 2 carbon atoms).

In the compound represented by formula Rf-Q-X—$NR_2$, each R is independently hydrogen, alkyl (e.g., having up to 4 carbon atoms such as methyl, ethyl, n-propyl, isopropyl, n-butyl, or isobutyl), or hydroxalkyl (e.g., hydroxyethyl, hydroxypropyl, or hydroxybutyl). In some embodiments, each R is hydrogen. In some embodiments, each R is methyl.

In some embodiments of the method disclosed herein, the fluorinated amine is represented by formula Rf—$SO_2N(R')$—X—$NH_2$, wherein Rf is perfluoroalkyl having up to 6 (in some embodiments, up to 4) carbon atoms, R' is methyl, ethyl, or —X—$NH_2$, and each X is independently alkylene having up to 4 (in some embodiments, 3 or 2) carbon atoms.

In some embodiments of the method disclosed herein, the fluorinated amine is represented by formula Rf—C(O)—N(R')—X—$NH_2$, wherein Rf is perfluoropolyether having at least 10 fluorinated carbon atoms and at least three —O— groups, R' is methyl, ethyl, or —X—$NH_2$, and X is alkylene having up to 4 (in some embodiments, 3 or 2) carbon atoms.

The present disclosure provides a compound represented by formula Rf'—SO$_2$N(—R$^2$—NH$_2$)$_2$ or a salt thereof, wherein Rf' is fluoroalkyl having up to 10 carbon atoms; and each R$^2$ is independently a straight chain or branched alkylene having 2 or 3 in-chain carbon atoms and up to 10 carbon atoms total. The compound may be useful, for example, as a fluorinated amine in the method of modifying the surface of a hydrocarbon-bearing formation disclosed herein. In some embodiments, Rf' is fluoroalkyl having up to 8, 6, or 4 carbon atoms (e.g., in a range from 2 to 10, 4 to 8, or 2 to 6 carbon atoms). Exemplary Rf' groups include trifluoromethyl, perfluoroethyl, 1,1,2,2-tetrafluoroethyl, 2-chlorotetrafluoroethyl, perfluoro-n-propyl, perfluoroisopropyl, perfluoro-n-butyl, 1,1,2,3,3,3-hexafluoropropyl, perfluoroisobutyl, perfluoro-sec-butyl, or perfluoro-tert-butyl, perfluoro-n-pentyl, pefluoroisopentyl, perfluorohexyl, perfluoroheptyl, or perfluorooctyl. In some embodiments, Rf' is perfluorobutyl (e.g., perfluoro-n-butyl, perfluoroisobutyl, or perfluoro-sec-butyl). In some embodiments, Rf' is perfluoropropyl (e.g., perfluoro-n-propyl). Rf' may be a mixture of fluoroalkyl groups. In R$^2$ is a straight chain or branched alkylene having a total of up to 8, 6, 4, or 3 carbon atoms. In some embodiments R$^2$ is —CH$_2$—CH$_2$—, and in some embodiments, R$^2$ is —CH$_2$—CH$_2$—CH$_2$—.

In some embodiments, the fluorinated amine is polymeric. In some embodiments, the polymeric fluorinated amine is represented by formula I:

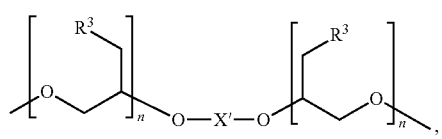

(I)

wherein each R$^3$ is independently —X"—Rf' or —NR$_2$, wherein each R independently is as defined above in any of the embodiments of R associated with non-polymeric fluorinated amines, with the proviso that the polymeric fluorinated amine contains at least one —X"—Rf' group and at least one —NR$_2$ group. In the polymeric fluorinated amine, Rf' is fluoroalkyl having up to 10 carbon atoms (e.g., up to 8, 6, or 4 carbon atoms, for example, in a range from 2 to 10, 4 to 8, or 2 to 6 carbon atoms). Exemplary Rf' groups include trifluoromethyl, perfluoroethyl, 1,1,2,2-tetrafluoroethyl, 2-chlorotetrafluoroethyl, perfluoro-n-propyl, perfluoroisopropyl, perfluoro-n-butyl, 1,1,2,3,3,3-hexafluoropropyl, perfluoroisobutyl, perfluoro-sec-butyl, or perfluoro-tert-butyl, perfluoro-n-pentyl, pefluoroisopentyl, perfluorohexyl, perfluoroheptyl, or perfluorooctyl. In some embodiments, Rf' is perfluorobutyl (e.g., perfluoro-n-butyl, perfluoroisobutyl, or perfluoro-sec-butyl). In some embodiments, Rf' is perfluoropropyl (e.g., perfluoro-n-propyl). Rf' may be a mixture of fluoroalkyl groups.

In formula I, each X" is independently —N(R")SO$_2$—*, —N(R")CO—*, —O—C$_p$H$_{2p}$—*, —S—C$_p$H$_{2p}$—*, or —C$_q$H$_{2q}$—, with the * indicating the position to which the Rf is attached, wherein R" is hydrogen or alkyl having 1 to 4 carbon atoms, and wherein p has a value from 0 to 6 (i.e., 0, 1, 2, 3, 4, 5, or 6). In some embodiments, each X" is independently —N(R")SO$_2$— or —N(R")CO—. In some of these embodiments, R" is alkyl having 1 to 4 carbon atoms (e.g., methyl or ethyl). In some embodiments, X" is —N(R")SO$_2$—, and R" is methyl or ethyl. In some embodiments, each X" is independently —O—C$_p$H$_{2p}$— or —S—C$_p$H$_{2p}$—.

In some embodiments, X" is —O—C$_p$H$_{2p}$—. In some of these embodiments, p is 1; in other of these embodiments, p is 2. In yet other of these embodiments, p is 0.

In the polymeric fluorinated amines, X' is alkylene that is optionally interrupted by one or more —O— groups. In some embodiments, X is alkylene (e.g., having at least 2 carbon atoms). In some embodiments, X' is polyalkyleneoxy with alkyleneoxy groups having from 2 to 4 (e.g., 2 to 3) carbon atoms. The polyalkyleneoxy can be a mixture of groups, for example, ethyleneoxy and propyleneoxy. In some embodiments, X' is polyethyleneoxy (i.e., a block of repeating ethylene oxide units). The block of repeating ethylene oxide units may have a number average molecular weight of at least 200, 300, 500, 700, or even at least 1000 grams per mole up to 2000, 4000, 5000, 8000, 10000, or even up to 15000 grams per mole. In some embodiments, X is represented by formula -[EO]$_f$-[HAO]$_g$-[EO]$_f$- or —[HAO]$_g$-[EO]$_f$-[HAO]$_g$—, wherein EO represents —CH$_2$CH$_2$O—; each HAO independently represents —CH(CH$_3$)CH$_2$O—, —CH$_2$CH(CH$_3$)O—, —CH(CH$_2$CH$_3$)CH$_2$O—, —CH$_2$CH(CH$_2$CH$_3$)O—, or —CH$_2$C(CH$_3$)$_2$O—; each f is independently a number from 1 to about 250 (e.g., 1 to 150, 1 to 100, 1 to 75, or 1 to 50); and each g is independently a number from 0 to about 55 (e.g., 0 to 45, 1 to 35, or 1 to 25). In some embodiments, each HAO independently represents —CH(CH$_3$)CH$_2$O— or —CH$_2$CH(CH$_3$)O—. In some embodiments, g is in a range of from 1 to 55 and the ratio f/g has a value of from at least 0.5, 0.75, 1 or 1.5 to 2.5, 2.7, 3, 4, 5, or more.

Polymeric fluorinated amines wherein X' is polyalkyleneoxy may be useful, for example, when the hydrocarbon-bearing formation with a surface comprising a carbonate further comprises a layer or other portion that is siliciclastic (e.g., shale, conglomerate, diatomite, sand, and sandstone) and/or when the hydrocarbon-bearing formation has at least one fracture that contains a plurality of proppants (e.g., sand or ceramic proppants). A plurality of alkyleneoxy groups may allow the polymeric fluorinated amines to interact with (e.g., adsorb onto) the surface of a siliciclastic layer or a plurality of proppants and modify the wettability of the surface.

In the polymeric fluorinated amines represented by formula I, each n is independently a value from 2 to 10. In some embodiments, n+n is up to 10. In some embodiments, n+n is at least 2, 3, 4, 5 6, 7, 8, 9, or even at least 10.

In some embodiments of formula I, at least some of the R$^3$ groups may be quaternary ammonium groups

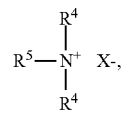

wherein R$^4$ and R$^5$ are each independently alkyl. In some embodiments, each R$^4$ is independently alkyl having 1 to 4 carbon atoms (e.g., methyl, ethyl, n-propyl, isopropyl, n-butyl, or isobutyl). In some embodiments, R$^5$ is alkyl having 1 to 20 (1 to 15, 1 to 10, or even 1 to 6) carbon atoms. X— is independently a counter anion. Typical counter anions include halides (i.e., fluoride, chloride, bromide, and iodide), organic acid anions (e.g., acetate, propionate, laurate, palmitate, stearate, or citrate), organic sulfonic or sulfuric acid anions (e.g., alkyl sulfates or alkanesulfonates), nitrate, and tetrafluoroborate. The organic acid anions and sulfonic acid anions may be partially fluorinated or perfluorinated. In some embodiments, X— is chloride, bromide, or iodide (i.e., Cl—, Br—, or I—). These quaternary ammonium groups may be useful, for example, when the hydrocarbon-bearing formation with a surface comprising a carbonate further comprises a layer or other portion that is siliciclastic (e.g., shale, conglomerate, diatomite, sand, and sandstone) and/or when the hydrocarbon-bearing formation has at least one fracture that contains a plurality of proppants (e.g., sand or ceramic proppants). The cationic groups may allow the polymeric fluorinated amines to interact with (e.g., adsorb onto) the surface of a siliciclastic layer or a plurality of proppants and modify the wettability of the surface.

In some embodiments wherein the fluorinated amine is polymeric, the polymeric fluorinated amine comprises (e.g., at least 2, 3, 4, 5, 6, 7, 8, 9, 10, 15, or even at least 20 up 30, 35, 40, 45, 50, 100, or even up to 200) first divalent units independently represented by formula:

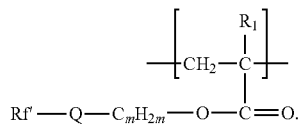

For divalent units having this formula, Q is a bond or —SO$_2$N(R")—, wherein R" is hydrogen or alkyl having 1 to 4 carbon atoms (e.g., methyl, ethyl, n-propyl, isopropyl, n-butyl, or isobutyl). In some embodiments, Q is a bond. In some embodiments, Q is —SO$_2$N(R")—. In some of these embodiments, R" is methyl or ethyl. m is an integer from 1 to 11 (i.e., 1, 2, 3, 4, 5, 6, 7, 8, 9, 10, or 11). In some of these embodiments, m is 1; in other of these embodiments, m is 2. In some embodiments wherein Q is —SO$_2$N(R")—, m is an integer from 2 to 11, 2 to 6, or 2 to 4. In some embodiments wherein Q is a bond, m is an integer from 1 to 6, 1 to 4, or 1 to 2. In embodiments wherein Q is a bond, it should be understood that the first divalent units may also be represented by formula:

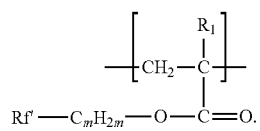

In embodiments wherein Q is —SO$_2$N(R")—, it should be understood that the first divalent units may also be represented by formula:

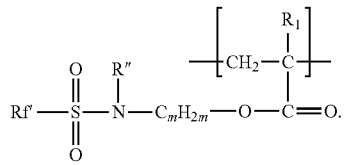

For any of the embodiments of the first divalent units having Rf' groups, each Rf' is independently as defined above in any of the aforementioned embodiments of Rf' in polymeric fluorinated amines of formula I. For any of the embodiments of the first divalent units, R$^1$ is hydrogen or methyl. In some embodiments, R$^1$ is hydrogen. In some embodiments, R$^1$ is methyl. For some embodiments of polymeric fluorinated amines useful for practicing the present disclosure, the first divalent units are present in a range from 15 to 80, 20 to 80, 25 to 75, or 25 to 65 percent by weight, based on the total weight of the polymeric fluorinated amine.

In embodiments wherein the fluorinated amine is polymeric and comprises the first divalent units, the polymeric fluorinated amine further comprises (e.g., at least 2, 3, 4, 5, 6, 7, 8, 9, 10, 15, or even at least 20 up 30, 35, 40, 45, 50, 100, or even up to 200) second divalent units independently represented by formula:

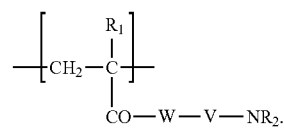

In these second divalent units, W is —O—, —S—, or —N(R")—, wherein R" is alkyl having 1 to 4 carbon atoms (e.g., methyl, ethyl, n-propyl, isopropyl, n-butyl, or isobutyl). In some embodiments, W is —O—. V is alkylene that is optionally interrupted by at least one ether linkage or amine linkage and optionally substituted by hydroxyl. In some embodiments, V is alkylene that is optionally interrupted by at least one ether linkage. In some embodiments, V is alkylene having 2 to 10, 2 to 8, 2 to 6, 3 to 6, 3 to 8, or 3 to 10 carbon atoms. In these second divalent units, each R and R$^1$ is independently as defined above in any of the aforementioned embodiments of R and R$^1$. In some embodiments, the fluorinated amine comprises more than 3 of the second divalent units. In some embodiments, the second divalent units are present in a range from 20 to 85, 25 to 85, 25 to 80, or 30 to 70 percent by weight, based on the total weight of the polymeric fluorinated amine. In some embodiments, each of the first divalent units and the second divalent units are each present in a range from 35 to 65 percent by weight, based on the total weight of the polymeric fluorinated amine. For some embodiments, the mole ratio of first divalent units to second divalent units in the polymer fluorinated amine is 4:1, 3:1, 2:1, 1:1, 1:2, or 1:3.

In some embodiments, the polymeric fluorinated amine comprises third divalent units represented by formula:

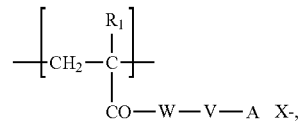

wherein W, V, and R$^1$ are as defined above in the description of the second divalent units. In the third divalent units, A is

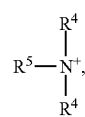

wherein R$^4$ and R$^5$ are each independently alkyl. In some embodiments, each R$^4$ is independently alkyl having 1 to 4 carbon atoms (e.g., methyl, ethyl, n-propyl, isopropyl, n-butyl, or isobutyl). In some embodiments, R$^5$ is alkyl having 1 to 20 (1 to 15, 1 to 10, or even 1 to 6) carbon atoms.

In the third divalent units, X— is independently a counter anion. Typical counter anions include halides (i.e., fluoride, chloride, bromide, and iodide), organic acid anions (e.g., acetate, propionate, laurate, palmitate, stearate, or citrate), organic sulfonic or sulfuric acid anions (e.g., alkanesulfonates or alkyl sulfates), nitrate, and tetrafluoroborate. The organic acid anions and sulfonic acid anions may be partially fluorinated or perfluorinated. In some embodiments, X— is chloride, bromide, or iodide (i.e., Cl—, Br—, or I—).

These third divalent units may be useful, for example, when the hydrocarbon-bearing formation with a surface comprising a carbonate further comprises a layer or other portion that is siliciclastic (e.g., shale, conglomerate, diatomite, sand, and sandstone) and/or when the hydrocarbon-bearing formation has at least one fracture that contains a plurality of proppants (e.g., sand or ceramic proppants). The cationic groups may allow the polymeric fluorinated amines to interact with (e.g., adsorb onto) the surface of a siliciclastic layer or a plurality of proppants and modify the wettability of the surface. In some embodiments, polymers fluorinated amines having first, second, and optionally third divalent units may further comprise a plurality of alkyleneoxy units (e.g., having 2 to 6 carbon atoms, for example, ethyleneoxy or propyleneoxy).

For some embodiments of polymeric fluorinated amines useful for practicing the present disclosure (e.g., including amines of formula I and amines having first and second divalent units as described above), the weight average molecular weight of the polymeric fluorinated amines is in a range from 1500, 2000, 2500, or even 3000 grams per mole up to 10,000, 20,000, 25,000, 30,000, 40,000, 50,000, 60,000, 70,000, 80,000, 90,000, or 100,000 grams per mole although higher molecular weights may also be useful.

The present disclosure provides a method of making a fluorinated amine that is useful for practicing the method of treating a hydrocarbon-bearing formation disclosed herein. The method includes combining a fluoroalkyl compound having an acidic hydrogen and cyclic imidate represented by formula

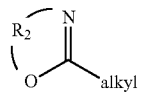

to provide a fluorinated amide and hydroylzing the fluorinated amide to provide the fluorinated amine. In some embodiments, the fluoroalkyl compound and the cyclic imidate are combined in the presence of base (e.g. sodium carbonate). The reaction may be carried out at room temperature but it is typically heated at an elevated temperature (e.g., at least 100° C., 110° C., or 125° C. and up to about 175° C., 160° C., or 150° C.). Upon combining the fluoroalkyl compound, the cyclic imidate, and base, the reaction may be heated, for example, in a range from 100° C. to 175° C., 110° C. to 160° C., or 125° C. to 150° C. Hydrolyzing the fluorinated amide may be carried out, for example, under acidic conditions, optionally at an elevated temperature. For example, the fluorinated amide may be combined with aqueous hydrochloric acid and heated at a temperature up to the reflux temperature of the mixture.

Useful fluorinated compounds having an acidic hydrogen include Rf'—$SO_2N(R')$—H or Rf'—$CH_2OH$, wherein Rf' is fluoroalkyl having up to 10 carbon atoms, and wherein R' is hydrogen, alkyl having up to 4 carbon atoms, or —$R^2$—$NR_2$. In some embodiments, Rf' is fluoroalkyl having up to 8, 6, or 4 carbon atoms (e.g., in a range from 2 to 10, 4 to 8, or 2 to 6 carbon atoms). Exemplary Rf' groups include trifluoromethyl, perfluoroethyl, 1,1,2,2-tetrafluoroethyl, 2-chlorotetrafluoroethyl, perfluoro-n-propyl, perfluoroisopropyl, perfluoro-n-butyl, 1,1,2,3,3,3-hexafluoropropyl, perfluoroisobutyl, perfluoro-sec-butyl, or perfluoro-tert-butyl, perfluoro-n-pentyl, pefluoroisopentyl, perfluorohexyl, perfluoroheptyl, or perfluorooctyl. In some embodiments, Rf' is perfluorobutyl (e.g., perfluoro-n-butyl, perfluoroisobutyl, or perfluoro-sec-butyl). In some embodiments, Rf' is perfluoropropyl (e.g., perfluoro-n-propyl). Rf' may be a mixture of fluoroalkyl groups. In any of these embodiments, $R^2$ is a straight chain or branched alkylene having up to 10 (in some embodiments, up to 8, 6, 4, or 3) carbon atoms, and wherein the $R^2$ group together with the —O—C(=N)— group form a five- or six-membered ring. When these fluorinated compounds are used as starting materials, the fluorinated amide is represented by formula Rf'—$SO_2N(R')$—$R^2$—N—C(O)-alkyl or Rf'—$CH_2O$—$R^2$—N—C(O)-alkyl, which provides fluorinated amines Rf'—$SO_2N(R')$—$R^2$—$NH_2$ or Rf'—$CH_2O$—$R^2$—$NH_2$ after hydrolysis, wherein Rf' is as defined above. In any of these embodiments of fluorinated amides or amines, $R^2$ is a straight chain or branched alkylene having 2 or 3 in-chain carbon atoms and a total of up to 10 (in some embodiments, up to 8, 6, 4, or 3) carbon atoms. In some embodiments of the cyclic imidates, fluorinated amides, and fluorinated amines, $R^2$ is —$CH_2$—$CH_2$—, and in some embodiments, $R^2$ is —$CH_2$—$CH_2$—$CH_2$—. Exemplary useful cyclic imidates include 2-ethyl-2-oxazoline.

Fluorinated amines can be prepared, for example, by other known methods. For example, a compound of formula Rf—$SO_2N(R')$—H can be treated with acrylonitrile, and the resulting nitrile can be reduced to an amine. Or a compound of formula Rf—$SO_2N(R')$—H can be treated with dimethylaminoethyl chloride hydrochloride, for example, according to the procedure described in the Examples of U.S. Pat. No. 7,164,041 (Moore et al.). Also, a compound of formula Rf—$SO_2N(R')$—$CH_2$—$CH_2$—OH, for example, $C_4F_9SO_2N(CH_3)$—$CH_2$—$CH_2$—OH prepared in Example 2 of U.S. Pat. No. 6,664,354 (Savu et al.), can be subjected to an arylsulfonation and amination sequence to provide a fluorinated amine. In other examples, fluorinated sulfonyl fluorides (e.g., perfluoro-1-butanesulfonyl fluoride, which is available from Sigma-Aldrich, St. Louis, Mo., and perfluoro-1-hexanesulfonyl fluoride) and fluorinated carboxylic acids or their derivatives can be treated with an amine having formula $NH_2$—W—$NR_2$ (e.g., 3-(dimethylamino) propylamine).

Some fluorinated carboxylic acids and fluorinated acid fluorides that may be useful for reaction with an amine having formula $NH_2$—W—$NR_2$ are commercially available (e.g., carboxylic acids of formula $CF_3$—[O—$CF_2$]$_{1-3}$C(O)OH, available, for example, from Anles Ltd., St. Petersburg, Russia, and acid fluorides of formulas $C_2F_5$—O—$(CF_2)_2$—C(O)F, $C_3F_7$—O—$(CF_2)_2$—C(O)F and $CF_3CF_2$—O—$CF_2CF_2$—O—$CF_2$C(O)F, available, for example, from Exfluor, Round Rock, Tex.). In some embodiments of the methods and the hydrocarbon-bearing formations disclosed herein, Rf is a perfluorinated polyether group of formula: $CF_3CF_2CF_2$—O—[CF($CF_3$)$CF_2O$]$_x$—CF($CF_3$)—, wherein x is as defined above. Fluorinated acids of this type can be prepared by oligomerization of hexafluoroproylene oxide to provide a perfluoropolyether carbonyl fluoride.

Fluorinated carboxylic acids that are useful for preparing partially fluorinated polyfluoroether amines disclosed herein can also be prepared, for example, starting from fluorinated ether olefins represented by formula $Rf^e$—(O)$_f$—CF=$CF_2$, wherein $Rf^e$ represents a partially or fully fluorinated alkyl group having from 1 to 10 carbon atoms and optionally interrupted with at least one oxygen atom, and t is 0 or 1, with the proviso that when t is 0, then $Rf^e$ is interrupted with at least one oxygen atom. Conditions for the preparation of compounds of formula $Rf^e$—(O)$_t$—CHF—CF$_2$—C(O)OH, CF$_3$—(CF$_2$)$_2$—O—CF$_2$—C(O)—CH$_3$, and CF$_3$—O—(CF$_2$)$_3$—O—CF$_2$—C(O)—CH$_3$, are described, for example, in U.S. Pat. App. No. 2007/0015864 (Hintzer et al.). Fluorinated carboxylic acids represented by formula CF$_3$CFH—O—(CF$_2$)$_{p'}$—C(O)OH, wherein p' is 1 to 6, and their derivatives can be prepared, for example, by decarbonylation of difunctional perfluorinated acid fluoride according to the reaction:

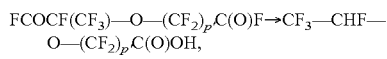

FCOCF(CF$_3$)—O—(CF$_2$)$_p$C(O)F→CF$_3$—CHF—O—(CF$_2$)$_p$C(O)OH, using conditions, e.g., in U.S. Pat. No. 3,555,100 (Garth et al.).

Polymeric fluorinated amines useful for practicing the present disclosure can be prepared, for example, by polymerizing a mixture of components typically in the presence of an initiator. By the term "polymerizing" it is meant forming a polymer or oligomer that includes at least one identifiable structural element due to each of the components. Typically the polymer or oligomer that is formed has a distribution of molecular weights and compositions.

Polymeric fluorinated amines represented by formula I can be prepared by ring-opening polymerization of oxirane rings with pendent fluoroalkyl groups (hereinafter, "fluorinated oxiranes") and epichlorohydrin with subsequent reaction of at least some of the resulting pendent chloromethyl groups with amines. Polymeric fluorinated amines represented by formula I can also be prepared by ring-opening polymerization of fluorinated oxiranes and oxirane rings with pendent protected amino groups (hereinafter, protected amine oxiranes) and subsequently deprotecting the amine. Some fluorinated oxiranes are available, for example, from commercial sources (e.g., 1H, 1H, 2H, 3H, 3H-perfluorononylene-1,2-oxide and 1H, 1H, 2H, 3H, 3H-perfluoroheptylene-1,2-oxide are available from ABCR GmbH & Co., Germany) Other fluorinated oxiranes can be prepared by conventional methods. For example, fluorinated alcohols and fluorinated sulfonamides can be treated with epichlorohydrin under basic conditions. Suitable fluorinated alcohols include trifluoroethanol, heptafluorobutanol, or nonafluorohexanol, which are commercially available, for example, from Sigma-Aldrich Corp., St. Louis, Mo. Suitable fluorinated sulfonamides include N-methylperfluorobutanesulfonamide and N-methylperfluorohexanesulfonamide, which can be prepared according to the methods described in Examples 1 and C6 of U.S. Pat. No. 6,664,534 (Savu et al.). Reactions of fluorinated alcohols or fluorinated sulfonamides with epichlorohydrin can be carried out, for example, in aqueous sodium hydroxide in the presence of a phase-transfer reagent such as methyltrialkyl(C8 to C10)ammonium chloride available from Sigma-Aldrich Corp. under the trade designation "ADOGEN 464" or in the presence of sodium hydride or sodium methoxide in a suitable solvent (e.g., tetrahydrofuran). Typically, reactions of fluorinated alcohols with epichlorohydrin are carried out at an elevated temperature (e.g., up to 40° C., 60° C., 70° C., or up to the reflux temperature of the solvent), but they may be carried out at room temperature. Some useful protected amine oxiranes are commercially available, e.g., 3-(dimethylamino)-1,2-epoxypropane methanesulfonic acid salt and 3-(N-tert-butoxycarbonylamino)-1,2-epoxypropane. Others can be prepared by conventional techniques.

Fluorinated oxiranes and amine oxiranes typically undergo ring-opening polymerization in the presence of Lewis Acid catalysts such as complexes of boron trifluoride (e.g., boron trifluoride etherate, boron trifluoride tetrahydropyran, and boron trifluoride tetrahydrofuran), phosphorous pentafluoride, antimony pentafluoride, zinc chloride, and aluminum bromide. The reaction can also be carried out in the presence of (CF$_3$SO$_2$)$_2$CH$_2$. Ring-opening polymerizations can be carried out neat or in a suitable solvent such as a hydrocarbon solvent (e.g., toluene) or a halogenated solvent (e.g., dichloromethane, carbon tetrachloride, trichloroethylene, or dichloroethane). The reactions can be carried out at or near room temperature or below (e.g., in a range from about 0° C. to 40° C.). The reactions can also be carried out above room temperature (e.g., up to 40° C., 60° C., 70° C., 90° C., or up to the reflux temperature of the solvent).

For polymeric fluorinated amines represented by formula I, the ring-opening polymerization is carried out in the presence of a monohydroxy alcohol or a diol represented by formula HO—X'—OH, wherein X' is as defined above. Compounds of formula HO—X'—OH include alkane diols (e.g., ethylene glycol, 1,4-butanediol, propylene glycol, 1,3-isobutenediol, 1,5-pentanediol, or neopentyl glycol) and poly(ethylene glycols) of various molecular weights (e.g., number average molecular weights of at least 200, 300, or even 500 grams per mole up to 1000, 2000, 4000, 5000, 8000, 10000, or even 15000 grams per mole). Poly(ethylene glycols) are available, for example, from a variety of commercial sources (e.g., from Sigma-Aldrich and from Dow Chemical, Midland, Mich., under the trade designation "CARBOWAX").

For some embodiments of the polymeric fluorinated amines represented by formula I, the ring-opening polymerization is carried out in the presence of an oxirane comprising a plurality of groups having formula —CH$_2$CH$_2$O—. Such oxiranes can be prepared, for example, by reaction of a mono- or dihydroxy poly(ethylene glycol) with epichlorohydrin using any of the methods described above for the reaction of fluorinated alcohols or fluorinated sulfonamides with epichlorohydrin.

It may be useful in some cases to include another monomer in the ring-opening polymerization of substituted oxiranes. For example, tetrahydrofuran, tetrahydropyran, 2-methyltetrahydrofuran, 1,4-dioxane, 1,3-dioxane, 1,3-dioxalane, and trioxane can be used as co-monomers in the polymerization reaction. Caprolactone may also be used as a co-monomer in the polymerization reaction; however, in some embodiments, the fluorinated polymer is free of carboxylate ester groups. In addition, other hydroxyl-functional compounds may be used in the reaction such as a fluorinated alcohol (e.g., trifluoroethanol, heptafluorobutanol, nonafluorohexanol), a multi-functional alcohol (e.g., pentaerythritol, trimethylolpropane), a monohydroxy alcohol (e.g., methanol, ethanol, or n-propanol), or combinations thereof.

The polymeric fluorinated amines represented by formula I may be partially quaternized to provide a mixture of pendent —NR$_2$ groups and pendent quaternary ammonium groups

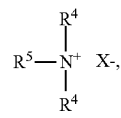

wherein R, R⁴, R⁵, and X'— are as defined above. Partial quaternization of a polymer of formula I comprising —NR₂ groups can be carried out using conventional techniques, for example, by reaction with an alkyl halide (e.g., bromobutane, bromoheptane, bromodecane, bromododecane, or bromohexadecane) in a suitable solvent.

Polymeric fluorinated amines that comprise first and second divalent units described above can also be prepared using conventional techniques. The components that are useful for preparing such polymer fluorinated amines include fluorinated free-radically polymerizable monomers independently represented by formula Rf'-Q-(C$_m$H$_{2m}$)—O—C(O)—C(R¹)=CH₂, wherein Rf', R¹, and m are as defined above.

Some compounds of Formula Rf'-Q-(C$_m$H$_{2m}$)—O—C(O)—C(R¹)=CH₂, are available, for example, from commercial sources (e.g., 3,3,4,4,5,5,6,6,6-nonafluorohexyl acrylate from Daikin Chemical Sales, Osaka, Japan, 3,3,4,4,5,5,6,6,6-nonafluorohexyl 2-methylacrylate from Indofine Chemical Co., Hillsborough, N.J., and 2,2,3,3,4,4,5,5-octafluoropentyl acrylate and methacrylate and 3,3,4,4,5,6,6,6-octafluoro-5-(trifluoromethyl)hexyl methacrylate from Sigma-Aldrich, St. Louis, Mo.). Others can be made by known methods (see, e.g., EP1311637 B1, published Apr. 5, 2006, for the preparation of 2,2,3,3,4,4,4-heptafluorobutyl 2-methylacrylate). Compounds wherein Q is —SO₂N(R")— can be made according to methods described in, e.g., U.S. Pat. No. 2,803,615 (Albrecht et al.) and U.S. Pat. No. 6,664,354 (Savu et al.), the disclosures of which, relating to free-radically polymerizable monomers and methods of their preparation.

Polymerizable monomers that may be useful for providing the second divalent units disclosed herein include compounds represented by formula R₂N—V—W—C(O)—C(R¹)=CH₂, wherein R, V, W, and R¹ are as defined above. Some compounds having these formulas are available, for example, from commercial sources (e.g., 2-(dimethylamino) ethyl acrylate, 2-(dimethylamino)ethyl methacrylate, 3-(dimethylamino)propyl acrylate, N-[3-(dimethylamino)-propyl]methacrylamide, and 2-(tert-butylamino)ethyl methacrylate from Sigma-Aldrich. Others can be prepared using conventional techniques.

For embodiments wherein the polymeric fluorinated amine comprising first and second divalent units further comprises third divalent units, the third divalent units may be incorporated into the polymer by adding monomers such as N,N-dimethylaminoethyl acrylate methyl chloride quaternary and N,N-dimethylaminoethyl methacrylate methyl chloride quaternary (available from Ciba Specialty Chemicals, Basel, Switzerland, under the trade designations "CIBA AGEFLEX FA1Q80MC" and "CIBA AGEFLEX FM1Q75MC", respectively). Tertiary amine-containing acrylates (e.g., 2-(dimethylamino)ethyl acrylate, 2-(dimethylamino)ethyl methacrylate, or 3-(dimethylamino)propyl acrylate) can be quaternized using conventional techniques, for example, by reaction with an alkyl halide (e.g., bromobutane, bromoheptane, bromodecane, bromododecane, or bromohexadecane) in a suitable solvent and optionally in the presence of a free-radical inhibitor to provide monomers useful incorporating the third divalent units. Quaternization can also be carried out, for example, after a tertiary amine-containing acrylate is polymerized, to provide a mixture of —NR₂ groups and pendent quaternary ammonium groups

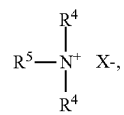

wherein R, R⁴, R⁵, and X'— are as defined above.

To prepare a polymeric fluorinated amine having first and second divalent units described above, free radical initiators may be used to initiate polymerization of the acrylate and methacrylate components. Examples of free-radical initiators include azo compounds (e.g., 2,2'-azobisisobutyronitrile (AIBN), 2,2'-azobis(2-methylbutyronitrile), or azo-2-cyanovaleric acid); hydroperoxides (e.g., cumene, tert-butyl or tert-amyl hydroperoxide); dialkyl peroxides (e.g., di-tert-butyl or dicumylperoxide); peroxyesters (e.g., tert-butyl perbenzoate or di-tert-butyl peroxyphthalate); diacylperoxides (e.g., benzoyl peroxide or lauryl peroxide). Useful photoinitiators include benzoin ethers (e.g., benzoin methyl ether or benzoin butyl ether); acetophenone derivatives (e.g., 2,2-dimethoxy-2-phenylacetophenone or 2,2-diethoxyacetophenone); and acylphosphine oxide derivatives and acylphosphonate derivatives (e.g., diphenyl-2,4,6-trimethylbenzoylphosphine oxide, isopropoxyphenyl-2,4,6-trimethylbenzoylphosphine oxide, or dimethyl pivaloylphosphonate). When heated or photolyzed such free-radical initiators fragment to generate free radicals which add to ethylenically unsaturated bonds and initiate polymerization.

Polymerization reactions may be carried out in any solvent suitable for organic free-radical polymerizations. The components may be present in the solvent at any suitable concentration, (e.g., from about 5 percent to about 90 percent by weight based on the total weight of the reaction mixture). Examples of suitable solvents include aliphatic and alicyclic hydrocarbons (e.g., hexane, heptane, cyclohexane), aromatic solvents (e.g., benzene, toluene, xylene), ethers (e.g., diethyl ether, glyme, diglyme, diisopropyl ether), esters (e.g., ethyl acetate, butyl acetate), alcohols (e.g., ethanol, isopropyl alcohol), ketones (e.g., acetone, methyl ethyl ketone, methyl isobutyl ketone), sulfoxides (e.g., dimethyl sulfoxide), amides (e.g., N,N-dimethylformamide, N,N-dimethylacetamide), halogenated solvents (e.g., methylchloroform, 1,1,2-trichloro-1,2,2-trifluoroethane, trichloroethylene or trifluorotoluene), and mixtures thereof.

Polymerization can be carried out at any temperature suitable for conducting an organic free-radical reaction. Particular temperature and solvents for use can be selected by those skilled in the art based on considerations such as the solubility of reagents, the temperature required for the use of a particular initiator, and the molecular weight desired. While it is not practical to enumerate a particular temperature suitable for all initiators and all solvents, generally suitable temperatures are in a range from about 30° C. to about 200° C.

Free-radical polymerizations may be carried out in the presence of chain transfer agents. Typical chain transfer agents that may be used in the preparation of polymers described herein include hydroxyl-substituted mercaptans (e.g., 2-mercaptoethanol, 3-mercapto-2-butanol, 3-mercapto-2-propanol, 3-mercapto-1-propanol, and 3-mercapto-1,2-propanediol (i.e., thioglycerol)); amino-substituted mercaptans (e.g., 2-mercaptoethylamine); difunctional mercaptans (e.g., di(2-mercaptoethyl)sulfide); and aliphatic mercaptans (e.g., octylmercaptan, dodecylmercaptan, and octadecylmercaptan).

Adjusting, for example, the concentration and activity of the initiator, the concentration of each of the reactive monomers, the temperature, the concentration of the chain transfer agent, and the solvent using techniques known in the art can control the molecular weight of a polyacrylate copolymer.

Polymeric fluorinated amines comprising at least first and second and optionally third divalent units may contain other divalent units, typically in weight percents up to 20, 15, 10, or 5 percent, based on the total weight of the polymeric fluorinated amine. These divalent units may be incorporated into the polymer chain by selecting additional components for the polymerization reaction such as alkyl acrylates and methacrylates (e.g., octadecyl methacrylate, lauryl methacrylate, butyl acrylate, isobutyl methacrylate, ethylhexyl acrylate, ethylhexyl methacrylate, methyl methacrylate, hexyl acrylate, heptyl acrylate, cyclohexyl methacrylate, or isobornyl acrylate); allyl esters (e.g., allyl acetate and allyl heptanoate); vinyl ethers or allyl ethers (e.g., cetyl vinyl ether, dodecylvinyl ether, 2-chloroethylvinyl ether, or ethylvinyl ether); alpha-beta unsaturated nitriles (e.g., acrylonitrile, methacrylonitrile, 2-chloroacrylonitrile, 2-cyanoethyl acrylate, or alkyl cyanoacrylates); alpha-beta-unsaturated carboxylic acid derivatives (e.g., allyl alcohol, allyl glycolate, acrylamide, methacrylamide, n-diisopropyl acrylamide, or diacetoneacrylamide); styrene and its derivatives (e.g., vinyltoluene, alpha-methylstyrene, or alpha-cyanomethyl styrene); olefinic hydrocarbons which may contain at least one halogen (e.g., ethylene, propylene, isobutene, 3-chloro-1-isobutene, butadiene, isoprene, chloro and dichlorobutadiene, 2,5-dimethyl-1,5-hexadiene, and vinyl and vinylidene chloride); and hydroxyalkyl-substituted polymerizable compounds (e.g., 2-hydroxyethyl methacrylate). Other divalent units containing pendent fluorinated groups include those derived from vinyl ethers, vinyl esters, allyl esters, vinyl ketones, styrene, vinyl amide, and acrylamides.

In some embodiments of the method of modifying a surface of a hydrocarbon-bearing formation disclosed herein, contacting the surface of the of the hydrocarbon-bearing formation comprises introducing a treatment composition comprising solvent and at least one of the fluorinated amine or a salt thereof into the hydrocarbon-bearing formation. In some embodiments, the treatment composition comprises the fluorinated amine. In some embodiments, the treatment composition comprises a salt of the fluorinated amine. Typically, in treatment compositions useful for practicing any of the methods described herein, the fluorinated amine or salt thereof is present in the treatment composition in an amount of at least 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.5, 1, 1.5, 2, 3, 4, or 5 percent by weight, up to 5, 6, 7, 8, 9, or 10 percent by weight, based on the total weight of the composition. For example, the amount of the fluorinated amine or salt thereof in the treatment compositions may be in a range of from 0.01 to 10, 0.1 to 10, 0.1 to 5, 1 to 10, or even in a range from 1 to 5 percent by weight, based on the total weight of the composition. Lower and higher amounts of the fluorinated amine or salt thereof in the treatment compositions may also be used, and may be desirable for some applications.

Treatment compositions useful for practicing the present disclosure typically comprise solvent. Examples of useful solvents for the method disclosed herein include organic solvents, water, easily gasified fluids (e.g., ammonia, low molecular weight hydrocarbons, and supercritical or liquid carbon dioxide), and combinations thereof. In some embodiments, the solvent is a water-miscible solvent (i.e., the solvent is soluble in water in all proportions). Examples of organic solvents include polar and/or water-miscible solvents, for example, monohydroxy alcohols having from 1 to 4 or more carbon atoms (e.g., methanol, ethanol, isopropanol, propanol, or butanol); polyols such as glycols (e.g., ethylene glycol or propylene glycol), terminal alkanediols (e.g., 1,3-propanediol, 1,4-butanediol, 1,6-hexanediol, or 1,8-octanediol), polyglycols (e.g., diethylene glycol, triethylene glycol, dipropylene glycol, or poly(propylene glycol)), triols (e.g., glycerol, trimethylolpropane), or pentaerythritol; ethers such as diethyl ether, methyl t-butyl ether, tetrahydrofuran, p-dioxane, or polyol ethers (e.g., glycol ethers (e.g., ethylene glycol monobutyl ether, diethylene glycol monomethyl ether, dipropylene glycol monomethyl ether, propylene glycol monomethyl ether, 2-butoxyethanol, or those glycol ethers available under the trade designation "DOWANOL" from Dow Chemical Co., Midland, Mich.)); ketones (e.g., acetone or 2-butanone); and combinations thereof. In some embodiments, the treatment composition comprises at least one of water, a monohydroxy alcohol, an ether, a ketone, a glycol, a glycol ether, or supercritical carbon dioxide.

In some embodiments of the treatment compositions and methods of modifying a surface disclosed herein, the solvent comprises at least one of a polyol or polyol ether independently having from 2 to 25 (in some embodiments, 2 to 15, 2 to 10, 2 to 9, or 2 to 8) carbon atoms. In some embodiments, the solvent comprises a polyol. The term "polyol" refers to an organic molecule consisting of C, H, and O atoms connected one to another by C—H, C—C, C—O, O—H single bonds, and having at least two C—O—H groups. In some embodiments, useful polyols have 2 to 25, 2 to 20, 2 to 15, 2 to 10, 2 to 8, or 2 to 6 carbon atoms. In some embodiments, the solvent comprises a polyol ether. The term "polyol ether" refers to an organic molecule consisting of C, H, and O atoms connected one to another by C—H, C—C, C—O, O—H single bonds, and which is at least theoretically derivable by at least partial etherification of a polyol. In some embodiments, the polyol ether has at least one C—O—H group and at least one C—O—C linkage. Useful polyol ethers may have from 3 to 25 carbon atoms, 3 to 20, 3 to 15, 3 to 10, 3 to 8, or from 5 to 8 carbon atoms. In some embodiments, the polyol is at least one of ethylene glycol, propylene glycol, poly(propylene glycol), 1,3-propanediol, or 1,8-octanediol, and the polyol ether is at least one of 2-butoxyethanol, diethylene glycol monomethyl ether, ethylene glycol monobutyl ether, dipropylene glycol monomethyl ether, or 1-methoxy-2-propanol. In some embodiments, the polyol and/or polyol ether has a normal boiling point of less than 450° F. (232° C.), which may be useful, for example, to facilitate removal of the polyol and/or polyol ether from a well after treatment. In some embodiments, the solvent comprises at least one of 2-butoxyethanol, ethylene glycol, propylene glycol, poly(propylene glycol), 1,3-propanediol, 1,8-octanediol, diethylene glycol monomethyl ether, ethylene glycol monobutyl ether, or dipropylene glycol monomethyl ether.

In some embodiments of treatment compositions and methods of modifying a surface disclosed herein, the solvent comprises at least one of water, a monohydroxy alcohol, an ether, or a ketone, wherein the monohydroxy alcohol, the ether, and the ketone each independently have up to 4 carbon atoms. Exemplary monohydroxy alcohols having from 1 to 4 carbon atoms include methanol, ethanol, n-propanol, isopropanol, 1-butanol, 2-butanol, isobutanol, and t-butanol. Exemplary ethers having from 2 to 4 carbon atoms include diethyl ether, ethylene glycol methyl ether, tetrahydrofuran, p-dioxane, and ethylene glycol dimethyl ether. Exemplary ketones having from 3 to 4 carbon atoms include acetone, 1-methoxy-2-propanone, and 2-butanone. In some embodiments, useful solvents for practicing the methods disclosed herein comprise at least one of methanol, ethanol, isopropanol, tetrahydrofuran, or acetone.

In some embodiments of the treatment compositions and methods disclosed herein, the treatment compositions comprise at least two organic solvents. In some embodiments, the solvent comprises at least one of a polyol or polyol ether independently having from 2 to 25 (in some embodiments, 2 to 15, 2 to 10, 2 to 9, or 2 to 8) carbon atoms and at least one of water, a monohydroxy alcohol, an ether, or a ketone, wherein the monohydroxy alcohol, the ether, and the ketone each independently have up to 4 carbon atoms. In these embodiments, in the event that a component of the solvent is a member of two functional classes, it may be used as either class but not both. For example, ethylene glycol monomethyl ether may be a polyol ether or a monohydroxy alcohol, but not as both simultaneously. In these embodiments, each solvent component may be present as a single component or a mixture of components. In some embodiments, treatment compositions useful for practicing the methods disclosed herein comprise at least one of a polyol or polyol ether independently having from 2 to 25 (in some embodiments, 2 to 15, 2 to 10, 2 to 9, or 2 to 8) carbon atoms and at least one monohydroxy alcohol having up to 4 carbon atoms.

For any of the embodiments of the treatment compositions and methods disclosed herein, wherein the treatment compositions comprise at least one of a polyol or polyol ether independently having from 2 to 25 (in some embodiments, 2 to 15, 2 to 10, 2 to 9, or 2 to 8) carbon atoms, the polyol or polyol ether is present in the composition in an amount of at least 50, 55, 60, or 65 percent by weight and up to 75, 80, 85, or 90 percent by weight, based on the total weight of the treatment composition. Typically, the solvents disclosed herein are capable of solubilizing more brine in the presence of a fluorinated amine than methanol, ethanol, propanol, butanol, or acetone alone. In some embodiments of the methods disclosed herein, the solvent comprises up to 50, 40, 30, 20, or 10 percent by weight of a monohydroxy alcohol having up to 4 carbon atoms, based on the total weight of the treatment composition.

Exemplary useful combinations of solvents useful for treatment compositions are disclosed in U.S. Pat. No. 7,585, 817 (Pope et al.).

The amount of solvent typically varies inversely with the amount of other components in treatment compositions useful for practicing the present disclosure. For example, based on the total weight of the treatment composition the solvent may be present in the composition in an amount of from at least 10, 20, 30, 40, or 50 percent by weight or more up to 60, 70, 80, 90, 95, 98, or 99 percent by weight, or more.

In some embodiments, the treatment composition further comprises a fluorinated polymeric nonionic surfactant comprising a plurality of alkyleneoxy groups. The plurality of alkyleneoxy groups typically includes alkyleneoxy groups having from 2 to 4 or 2 to 3 carbon atoms (e.g., —$CH_2CH_2O$—, —$CH(CH_3)CH_2O$—, —$CH_2CH(CH_3)$ O—, —$CH_2CH_2CH_2O$—, —$CH(CH_2CH_3)CH_2O$—, —$CH_2CH(CH_2CH_3)O$—, or —$CH_2C(CH_3)_2O$—). The plurality of alkyleneoxy groups may be in a poly(alkyleneoxy) segment comprising repeating alkyleneoxy units having from 2 to 4 or 2 to 3 carbon atoms. Useful nonionic fluorinated surfactants may include those having the following general formula $CF_3CF_2(CF_2CF_2)_{2-4}$—$CH_2CH_2O$ $(R^6O)_{x''}R^7$, where $(R^6O)_{x''}$ is a poly(alkyleneoxy) segment as described above, and $R^7$ is hydrogen or alkyl having up to 4 carbon atoms. Nonionic fluorinated surfactants having formula $CF_3CF_2(CF_2CF_2)_{2-4}$—$CH_2CH_2O(R^6O)_{x''}R^7$ are commercially available, for example, from E. I. du Pont de Nemours and Co., Wilmington, Del., under the trade designation "ZONYL".

Another type of suitable nonionic fluorinated surfactant is a polymeric surfactant comprising divalent units having formula:

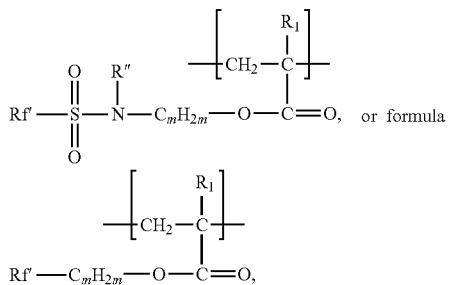

wherein each of Rf', R", m, and $R^1$ is independently defined as above in the description of polymeric fluorinated amines with first and second divalent units. Polymeric nonionic surfactants comprising divalent units having these formulas can be prepared, for example, using the methods described above for the preparation of polymeric fluorinated amines with first and second divalent units. Polymerizable monomers containing a plurality of alkyleneoxy groups include compounds of formulas HO-(EO)$_{f'}$—(PO)$_{g'}$-(EO)$_{f'}$—C (O)—C($R^1$)=$CH_2$, $R^8$O—(PO)$_{g'}$-(EO)$_{f'}$—(PO)$_{g'}$—C(O)— C($R^1$)=$CH_2$, $CH_2$=C($R^1$)—C(O)—O-(EO)$_{f'}$—(PO)$_{g'}$- (EO)$_{f'}$—C(O)—C($R^1$)=$CH_2$, and $CH_2$=C($R^1$)—C(O)— O—(PO)$_{g'}$-(EO)$_{f'}$—(PO)$_{g'}$—C(O)—C($R^1$)=$CH_2$, wherein f', g', $R^1$, $R^8$, EO, and PO are as defined below.

Some useful components containing a plurality of alkyleneoxy groups are available, for example, from commercial sources. For example, diethylene glycol diacrylate and tri(ethylene glycol) dimethacrylate can be obtained from general chemical suppliers (e.g., Sigma-Aldrich), and polyoxyalkylene glycol acrylates and diacrylates (e.g., $CH_2$=CHC (O)O($CH_2CH_2O)_{7-9}$H) are available from Nippon Oil & Fats Company, Tokyo, Japan under the trade designation "BLEMMER". Compounds of formulas HO-(EO)$_{f'}$— (PO)$_{g'}$-(EO)$_{f'}$—C(O)—C($R^1$)=$CH_2$ and $R^8$O—(PO)$_{g'}$- (EO)$_{f'}$—(PO)$_{g'}$—C(O)—C($R^1$)=$CH_2$ can also be prepared by known methods, for example, combining acryloyl chloride or acrylic acid with a polyethylene glycol or a monoalkyl ether thereof having a molecular weight of about 200 to 10,000 grams per mole (e.g., those available from Dow Chemical Company, Midland, Mich., under the trade designation "CARBOWAX") or a block copolymer of ethylene oxide and propylene oxide having a molecular weight of about 500 to 15000 grams per mole (e.g., those available from BASF Corporation, Ludwigshafen, Germany, under the trade designation "PLURONIC"). The reaction of acrylic acid with a poly(alkylene oxide) is typically carried out in the presence of an acid catalyst and a polymerization inhibitor at an elevated temperature in a suitable solvent; (see, e.g., Example 1 of U.S. Pat. No. 3,787,351 (Olson).

Poly(alkylene oxide)s terminated at both ends by hydroxyl groups can be reacted with two equivalents of acryloyl chloride or acrylic acid to provide compounds of formulas

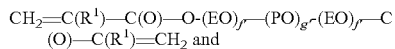

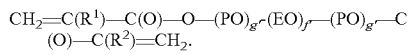

Some nonionic fluorinated polymeric surfactants useful for practicing the present disclosure are commercially available (e.g., from BYK Additives and Instruments, Wesel, Germany, under the trade designation "BYK-340", from Mason Chemical Company, Arlington Heights, Ill., under the trade designation "MASURF FS-2000", and from Ciba Specialty Chemicals, Basel, Switzerland, under the trade designation "CIBA EFKA 3600").

In some embodiments, the nonionic fluorinated polymeric surfactant comprises at least one divalent unit represented by formula:

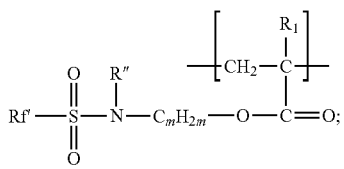

and
at least one divalent unit represented by formula:

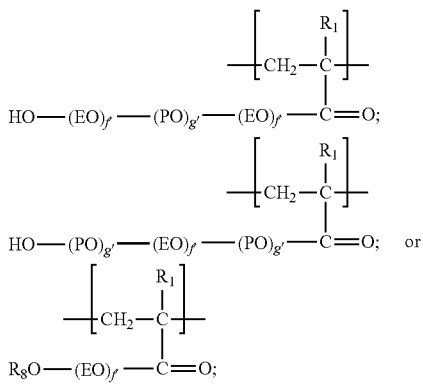

wherein
Rf' represents a perfluoroalkyl group having from 1 to 8 carbon atoms;
R", $R^1$, and $R^8$ are each independently hydrogen or alkyl having 1 to 4 carbon atoms;
n is from 2 to 10;
EO represents —$CH_2CH_2O$—;
each PO independently represents —$CH(CH_3)CH_2O$— or —$CH_2CH(CH_3)O$—;
each f' is independently a number from 1 to about 128; and
each g' is independently a number from 0 to about 55.

Treatment compositions comprising the fluorinated amine or salt thereof and a nonionic fluorinated polymeric surfactant comprising a plurality of alkyleneoxy groups may be useful, for example, when the hydrocarbon-bearing formation with a surface comprising a carbonate further comprises a layer or other portion that is siliciclastic (e.g., shale, conglomerate, diatomite, sand, and sandstone) and/or when the hydrocarbon-bearing formation has at least one fracture that contains a plurality of proppants (e.g., those described below). Nonionic fluorinated polymeric surfactants have been demonstrated to be useful for treating siliciclastic (e.g., sandstone) formations and fractured formations containing proppants (see, e.g., U.S. Pat. No. 7,585,817 (Pope et al.) and Int. Pat. App. Pub. No. WO 2008/118244 (Pope et al.)). However, such surfactants have been shown to have limited effectiveness on limestone; (see, e.g., Comparative Example A in Int. Pat. Appl. Pub. No. WO 2009/148831 (Sharma et al.), the disclosure of which example is incorporated herein by reference).

The ingredients for treatment compositions described herein including fluorinated amines or salts thereof, solvents, and optionally other agents (e.g., nonionic fluorinated polymeric surfactants) can be combined using techniques known in the art for combining these types of materials, including using conventional magnetic stir bars or mechanical mixer (e.g., in-line static mixer and recirculating pump).

Although not wishing to be bound by theory, it is believed that treatment methods according to the present disclosure will provide more desirable results when the treatment composition is homogenous at the temperature(s) encountered in the hydrocarbon-bearing formation. Whether the treatment composition is homogeneous at the temperature can depend on many variables (e.g., concentration of the fluorinated amine or salt thereof, solvent composition, brine concentration and composition, hydrocarbon concentration and composition, and the presence of other components (e.g., surfactants)). Without wanting to be bound by theory, it is believed that once the fluorinated amine contacts a hydrocarbon-bearing formation (e.g., downhole) comprising a carbonate surface, it will adsorb onto the formation and modify the wetting properties of the formation to cause an increase in at least one of the gas, oil, or water permeabilities in the formation.

In some embodiments of treatment methods according to the present disclosure, the hydrocarbon-bearing formation has brine. The brine present in the formation may be from a variety of sources including at least one of connate water, flowing water, mobile water, immobile water, residual water from a fracturing operation or from other downhole fluids, or crossflow water (e.g., water from adjacent perforated formations or adjacent layers in the formations). The brine may cause water blocking in the hydrocarbon-bearing formation. In some embodiments, the solvent in the treatment composition at least one of at least partially solubilizes or at least partially displaces brine in the hydrocarbon-bearing formation. In some embodiments, the brine has at least 2, 3, 4, 5, 6, 7, 8, 9, or even at least 10 weight percent dissolved salts (e.g., sodium chloride, calcium chloride, strontium chloride, magnesium chloride, potassium chloride, ferric chloride, ferrous chloride, and hydrates thereof), based on the total weight of the brine. Although not wanting to be bound by theory, it is believed that the effectiveness of the treatment methods disclosed herein for improving hydrocarbon productivity of a particular oil and/or gas well having brine accumulated in the near wellbore region will typically be determined by the ability of the treatment composition to dissolve or displace the quantity of brine present in the near wellbore region of the well without causing phase separation of the fluorinated amine or precipitation. Hence, at a given temperature greater amounts of treatment compositions having lower brine solubility (i.e., treatment compositions that can dissolve a relatively lower amount of brine) will typically be needed than in the case of treatment compositions having higher brine solubility and containing the same fluorinated amine or salt thereof at the same concentration.

In some embodiments of the treatment methods disclosed herein, when the fluorinated amine contacts the hydrocarbon-bearing formation, the hydrocarbon-bearing formation is substantially free of precipitated salt. As used herein, the term "substantially free of precipitated salt" refers to an amount of salt that does not interfere with the ability of the fluorinated amine to increase the gas permeability of the hydrocarbon-bearing formation. In some embodiments, "substantially free of precipitated salt" means that no precipitated salt is visually observed. In some embodiments, "substantially free of precipitated salt" is an amount of salt that is less than 5% by weight higher than the solubility product at a given temperature and pressure.

In some embodiments of treatment methods according to the present disclosure, combining the composition and the brine of the hydrocarbon-bearing formation at the temperature of the hydrocarbon-bearing formation does not result in the phase separation of the fluorinated amine. Phase behavior can be evaluated prior to treating the hydrocarbon-bearing formation with the composition by obtaining a sample of the brine from the hydrocarbon-bearing formation and/or analyzing the composition of the brine from the hydrocarbon-bearing formation and preparing an equivalent brine having the same or similar composition to the composition of the brine in the formation. The brine saturation level in a hydrocarbon-bearing formation can be determined using methods known in the art and can be used to determined the amount of brine that can be mixed with the treatment composition (i.e., the composition comprising solvent and the fluorinated amine or salt thereof). The brine and the treatment are combined (e.g., in a container) at the temperature and then mixed together (e.g., by shaking or stirring). The mixture is then maintained at the temperature for 15 minutes, removed from the heat, and immediately visually evaluated to see if it phase separates or if cloudiness or precipitation occurs. In some embodiments, the amount of brine that is added before phase separation occurs is at least 5, 10, 15, 20, 25, 30, 35, 40, 45, or at least 50% by weight, based on the total weight of brine and treatment composition combined in the phase behavior evaluation.

The phase behavior of the treatment composition and the brine can be evaluated over an extended period of time (e.g., 1 hour, 12 hours, 24 hours, or longer) to determine if any phase separation, precipitation (e.g., of salts or the fluorinated amine), or cloudiness is observed. By adjusting the relative amounts of brine (e.g., equivalent brine) and the treatment composition, it is possible to determine the maximum brine uptake capacity (above which phase separation or salt precipitation occurs) of the treatment composition at a given temperature. Varying the temperature at which the above procedure is carried out typically results in a more complete understanding of the suitability of compositions comprising solvents and fluorinated amines or salts thereof as treatment compositions for a given well. In additional to using a phase behavior evaluation, it is also contemplated that one may be able obtain the compatibility information, in whole or in part, by computer simulation or by referring to previously determined, collected, and/or tabulated information (e.g., in a handbook or a computer database).

In some embodiments of the method disclosed herein, the hydrocarbon-bearing formation has both liquid hydrocarbons and gas, and the hydrocarbon-bearing formation has at least a gas permeability that is increased after the hydrocarbon-bearing formation is contacted with the fluorinated amine. In some embodiments, the gas permeability after contacting the hydrocarbon-bearing formation with the fluorinated amine is increased by at least 5 percent (in some embodiments, by at least 10, 15, 20, 30, 40, 50, 60, 70, 80, 90, or 100 percent or more) relative to the gas permeability of the formation before treating the formation with the composition. In some embodiments, the gas permeability is a gas relative permeability. In some embodiments, the liquid (e.g., oil or condensate) permeability in the hydrocarbon-bearing formation is also increased (in some embodiments, by at least 5, 10, 15, 20, 30, 40, 50, 60, 70, 80, 90, or 100 percent or more) after treating the formation with the fluorinated amine.

Although it has been suggested that anionic compounds are useful for treating carbonate hydrocarbon-bearing formations (see, e.g., U.S. Pat. No. 4,585,065 (Penny et al.) and amines do not adsorb appreciably on sand (see, e.g., Canadian Patent 2,009,732, published on Aug. 11, 1990), it was unexpectedly found that the fluorinated amines disclosed herein can increase the gas and oil relative permeabilities in a carbonate formation (e.g., limestone) as shown in the Method Examples 1 and 2, below.

The hydrocarbon-bearing formation having both gas and liquid hydrocarbons may have gas condensate, black oil, or volatile oil and may comprise, for example, at least one of methane, ethane, propane, butane, pentane, hexane, heptane, octane, nonane, decane, or higher hydrocarbons. The term "black oil" refers to the class of crude oil typically having gas-oil ratios (GOR) less than about 2000 scf/stb (356 $m^3/m^3$). For example, a black oil may have a GOR in a range from about 100 (18), 200 (36), 300 (53), 400 (71), or even 500 scf/stb (89 $m^3/m^3$) up to about 1800 (320), 1900 (338), or 2000 scf/stb (356 $m^3/m^3$). The term "volatile oil" refers to the class of crude oil typically having a GOR in a range between about 2000 and 3300 scf/stb (356 and 588 $m^3/m^3$). For example, a volatile oil may have a GOR in a range from about 2000 (356), 2100 (374), or 2200 scf/stb (392 $m^3/m^3$) up to about 3100 (552), 3200 (570), or 3300 scf/stb (588 $m^3/m^3$). In some embodiments, the solvent (in the treatment composition) at least partially solubilizes or at least partially displaces the liquid hydrocarbons in the hydrocarbon-bearing formation.

Generally, for the treatment methods disclosed herein, the amounts of the fluorinated amine or salt thereof and solvent (and type of solvent) is dependent on the particular application since conditions typically vary between wells, at different depths of individual wells, and even over time at a given location in an individual well. Advantageously, treatment methods according to the present disclosure can be customized for individual wells and conditions.

Methods according to the present disclosure may be practiced, for example, in a laboratory environment (e.g., on a core sample (i.e., a portion) of a hydrocarbon-bearing formation or in the field (e.g., on a subterranean hydrocarbon-bearing formation situated downhole). Typically, the methods disclosed herein are applicable to downhole conditions having a pressure in a range from about 1 bar (100 kPa) to about 1000 bars (100 MPa) and have a temperature in a range from about 100° F. (37.8° C.) to 400° F. (204° C.) although the methods are not limited to hydrocarbon-bearing formations having these conditions. Those skilled in the art, after reviewing the instant disclosure, will recognize that various factors may be taken into account in practice of the any of the disclosed methods including the ionic strength of the brine, pH (e.g., a range from a pH of about 4 to about 10), and the radial stress at the wellbore (e.g., about 1 bar (100 kPa) to about 1000 bars (100 MPa)).

In the field, treating a hydrocarbon-bearing formation with a fluorinate amine or treatment composition described herein can be carried out using methods (e.g., by pumping under pressure) well known to those skilled in the oil and gas art. Coil tubing, for example, may be used to deliver the fluorinated amine or treatment composition to a particular geological zone of a hydrocarbon-bearing formation. In some embodiments of practicing the methods described herein it may be desirable to isolate a geological zone (e.g., with conventional packers) to be treated with the fluorinated amine or treatment composition.

Methods of modifying the surface of a hydrocarbon-bearing formation described herein are useful, for example on both existing and new wells. Typically, it is believed to be desirable to allow for a shut-in time after the hydrocarbon-bearing formations described herein are treated with fluorinated amines or treatment compositions. Exemplary shut-in times include a few hours (e.g., 1 to 12 hours), about 24 hours, or even a few (e.g., 2 to 10) days. After the treatment composition has been allowed to remain in place for a selected time, the solvents present in the treatment composition may be recovered from the formation by simply pumping fluids up tubing in a well as is commonly done to produce fluids from a formation.

In some embodiments of the method of modifying a surface of a hydrocarbon-bearing formation according to the present disclosure, the method comprises treating the hydrocarbon-bearing formation with a fluid prior to contacting the hydrocarbon-bearing formation with the fluorinated amine. In some embodiments, the fluid at least one of at least partially solubilizes or at least partially displaces the brine in the hydrocarbon-bearing formation. In some embodiments, the fluid at least partially solubilizes the brine. In some embodiments, the fluid at least partially displaces the brine. In some embodiments, the fluid at least one of at least partially solubilizes or displaces liquid hydrocarbons in the hydrocarbon-bearing formation. In some embodiments, the fluid is substantially free of fluorinated compounds. A fluid that is substantially free of fluorinated compound may be a fluid that has a fluorinated compound but in an amount insufficient to alter the wettability of, for example, a hydrocarbon-bearing formation under downhole conditions. A fluid that is substantially free of fluorinated compounds includes those that have a weight percent of such compounds as low as 0 weight percent. The fluid may be useful for decreasing the concentration of at least one of the salts present in the brine before introducing the fluorinated amine to the hydrocarbon-bearing formation. The change in brine composition may change the results of a phase behavior evaluation (e.g., the combination of a treatment composition disclosed herein with a first brine prior to the fluid preflush may result in phase separation or salt precipitation while the combination of the treatment composition with the brine after the fluid preflush may result in no phase separation or salt precipitation.)

In some embodiments of the method disclosed herein, the fluid comprises at least one of toluene, diesel, heptane, octane, or condensate. In some embodiments, the fluid comprises at least one of water, methanol, ethanol, or isopropanol. In some embodiments, the fluid comprises at least one of a polyol or polyol ether independently having from 2 to 25 carbon atoms. In some embodiments, useful polyols have 2 to 20, 2 to 15, 2 to 10, 2 to 8, or 2 to 6 carbon atoms. Exemplary useful polyols include ethylene glycol, propylene glycol, poly(propylene glycol), 1,3-propanediol, trimethylolpropane, glycerol, pentaerythritol, and 1,8-octanediol. In some embodiments, useful polyol ethers may have from 3 to 25 carbon atoms, 3 to 20, 3 to 15, 3 to 10, 3 to 8, or from 5 to 8 carbon atoms. Exemplary useful polyol ethers include diethylene glycol monomethyl ether, ethylene glycol monobutyl ether, dipropylene glycol monomethyl ether, 2-butoxyethanol, and 1-methoxy-2-propanol. In some embodiments, the fluid comprises at least one monohydroxy alcohol, ether, or ketone independently having up to four carbon atoms. In some embodiments, the fluid comprises at least one of nitrogen, carbon dioxide, or methane.

In some embodiments of the method and treated hydrocarbon-bearing formations disclosed herein, the hydrocarbon-bearing formation has at least one fracture. In some embodiments, fractured formations have at least 2, 3, 4, 5, 6, 7, 8, 9, or 10 or more fractures. As used herein, the term "fracture" refers to a fracture that is man-made. In the field, for example, fractures are typically made by injecting a fracturing fluid into a subterranean geological formation at a rate and pressure sufficient to open a fracture therein (i.e., exceeding the rock strength). Typically, fracturing refers to hydraulic fracturing, and the fracturing fluid is a hydraulic fluid. Fracturing fluids may or may not contain proppants. Unintentional fracturing can sometimes occur, for example, during drilling of a wellbore. Unintentional fractures can be detected (e.g., by fluid loss from the wellbore) and repaired. Typically, fracturing a hydrocarbon-bearing formation refers to intentionally fracturing the formation after the wellbore is drilled.

In some embodiments of the method and treated hydrocarbon-bearing formations disclosed herein, for example, wherein treating the formation with the fluorinated amine or treatment composition provides an increase in at least one of the gas permeability or the liquid permeability of the formation, the formation is a non-fractured formation (i.e., free of man-made fractures). The term "free of manmade fractures" refers to the hydrocarbon-bearing formation being free of fractures made by the intentional fracturing process described above. Advantageously, method disclosed herein typically provides an increase in at least one of the gas permeability or the hydrocarbon liquid permeability of the formation without fracturing the formation. However, hydrocarbon-bearing formations with a surface comprising a carbonate (e.g., limestone formations) typically have natural fractures. Natural fractures may be formed, for example, as part of a network of fractures.

In some embodiments of the treatment methods and articles disclosed herein, wherein the hydrocarbon-bearing formation has at least one fracture, the fracture has a plurality of proppants therein. Prior to delivering the proppants into a fracture, the proppants may be treated (e.g., with a fluorinated polymer) or untreated. In some embodiments, the treatment compositions useful for practicing the present disclosure may contain fluorinated polymers (e.g., nonionic fluorinated polymeric surfactants) that can be adsorbed on at least a portion of the plurality of proppants.

Exemplary proppants known in the art include those made of sand (e.g., Ottawa, Brady or Colorado Sands, often referred to as white and brown sands having various ratios), resin-coated sand, sintered bauxite, ceramics (i.e., glasses, crystalline ceramics, glass-ceramics, and combinations thereof), thermoplastics, organic materials (e.g., ground or crushed nut shells, seed shells, fruit pits, and processed wood), and clay. Sand proppants are available, for example, from Badger Mining Corp., Berlin, Wis.; Borden Chemical, Columbus, Ohio; and Fairmont Minerals, Chardon, Ohio. Thermoplastic proppants are available, for example, from the Dow Chemical Company, Midland, Mich.; and BJ Services, Houston, Tex. Clay-based proppants are available, for example, from CarboCeramics, Irving, Tex.; and Saint-Gobain, Courbevoie, France. Sintered bauxite ceramic proppants are available, for example, from Borovichi Refractories, Borovichi, Russia; 3M Company, St. Paul, Minn.; CarboCeramics; and Saint Gobain. Glass bubble and bead proppants are available, for example, from Diversified Industries, Sidney, British Columbia, Canada; and 3M Company.

In some embodiments of methods of treating fractured formations, the proppants form packs within a formation and/or wellbore. Proppants may be selected to be chemically compatible with the solvents and compositions described herein. The term "proppant" as used herein includes fracture proppant materials introducible into the formation as part of a hydraulic fracture treatment and sand control particulate introducible into the wellbore/formation as part of a sand control treatment such as a gravel pack or frac pack.

In some embodiments, methods according to the present disclosure include contacting the surface of the hydrocarbon-bearing formation with the fluorinated amine at least one of during fracturing or after fracturing the hydrocarbon-bearing formation.

In some embodiments of method disclosed herein wherein the hydrocarbon-bearing formation is a fractured formation, the amount of the composition introduced into the fractured formation is based at least partially on the volume of the fracture(s). The volume of a fracture can be measured using methods that are known in the art (e.g., by pressure transient testing of a fractured well). Typically, when a fracture is created in a hydrocarbon-bearing subterranean formation, the volume of the fracture can be estimated using at least one of the known volume of fracturing fluid or the known amount of proppant used during the fracturing operation. Coil tubing, for example, may be used to deliver the treatment composition to a particular fracture. In some embodiments, in practicing the methods disclosed herein it may be desirable to isolate the fracture (e.g., with conventional packers) to be treated with the treatment composition.

In some embodiments, wherein the formation treated according to the methods described herein has at least one fracture, the fracture has a conductivity, and after the composition treats at least one of the fracture or at least a portion of the plurality of proppants, the conductivity of the fracture is increased (e.g., by 25, 50, 75, 100, 125, 150, 175, 200, 225, 250, 275, or by 300 percent).

For methods of fracturing a hydrocarbon-bearing formation according to the present disclosure, the hydraulic fluid and/or the fluid comprising the plurality of proppants may be aqueous (e.g., a brine) or may contain predominantly organic solvent (e.g., an alcohol or a hydrocarbon). In some embodiments, it may be desirable for one or both of the fluids to include contain viscosity enhancing agents (e.g., polymeric viscosifiers), electrolytes, corrosion inhibitors, scale inhibitors, and other such additives that are common to a fracturing fluid.

Referring to FIG. 1, an exemplary offshore oil platform is schematically illustrated and generally designated 10. Semi-submersible platform 12 is centered over submerged hydrocarbon-bearing formation 14 located below sea floor 16. Subsea conduit 18 extends from deck 20 of platform 12 to wellhead installation 22 including blowout preventers 24. Platform 12 is shown with hoisting apparatus 26 and derrick 28 for raising and lowering pipe strings such as work string 30.

Wellbore 32 extends through the various earth strata including hydrocarbon-bearing formation 14. Casing 34 is cemented within wellbore 32 by cement 36. Work string 30 may include various tools including, for example, sand control screen assembly 38 which is positioned within wellbore 32 adjacent to hydrocarbon-bearing formation 14. Also extending from platform 12 through wellbore 32 is fluid delivery tube 40 having fluid or gas discharge section 42 positioned adjacent to hydrocarbon-bearing formation 14, shown with production zone 48 between packers 44, 46. When it is desired to treat the near-wellbore region of hydrocarbon-bearing formation 14 adjacent to production zone 48, work string 30 and fluid delivery tube 40 are lowered through casing 34 until sand control screen assembly 38 and fluid discharge section 42 are positioned adjacent to the near-wellbore region of hydrocarbon-bearing formation 14 including perforations 50. Thereafter, a fluorinated amine or treatment composition described herein is pumped down delivery tube 40 to progressively treat the near-wellbore region of hydrocarbon-bearing formation 14.

While the drawing depicts an offshore operation, the skilled artisan will recognize that the methods for treating a production zone of a wellbore are equally well-suited for use in onshore operations. Also, while the drawing depicts a vertical well, the skilled artisan will also recognize that methods according to the present disclosure are equally well-suited for use in deviated wells, inclined wells or horizontal wells.

Selected Embodiments of the Disclosure

In a first embodiment, the present disclosure provides a method of modifying a surface of a hydrocarbon-bearing formation, the method comprising contacting the surface of the hydrocarbon-bearing formation with a fluorinated amine, wherein the surface of the hydrocarbon-bearing formation comprises a carbonate.

In a second embodiment, the present disclosure provides a method according to the first embodiment, wherein contacting the surface of the hydrocarbon-bearing formation comprises introducing a treatment composition comprising solvent and at least one of the fluorinated amine or a salt thereof into the hydrocarbon-bearing formation.

In a third embodiment, the present disclosure provides a method according to the second embodiment, wherein the treatment composition comprises the fluorinated amine.

In a fourth embodiment, the present disclosure provides a method according to the second or third embodiment, wherein the treatment composition further comprises a fluorinated polymeric nonionic surfactant comprising a plurality of alkyleneoxy groups.

In a fifth embodiment, the present disclosure provides a method according to the second, third, or fourth embodiment, wherein the solvent comprises at least one of water, a monohydroxy alcohol, an ether, a ketone, a glycol, a glycol ether, or supercritical carbon dioxide.

In a sixth embodiment, the present disclosure provides a method according to any one of the first to fifth embodiments, wherein the fluorinated amine does not have polymeric repeating units comprising amine groups.

In a seventh embodiment, the present disclosure provides a method according to the sixth embodiment, wherein the fluorinated amine is non-polymeric.

In an eighth embodiment, the present disclosure provides a method according to any one of the first to seventh embodiments, wherein the fluorinated amine is represented by formula Rf-Q-X—NR$_2$ wherein Rf is a fluoroalkyl group optionally interrupted with at least one oxygen atom or a polyfluoropolyether having at least 10 fluorinated carbon atoms and at least three —O— groups;

Q is a bond, —SO₂N(R')—, or —C(O)N(R')—;

X is alkylene, arylene, alkylarylene, or arylalkylene, wherein alkylene, arylene, alkylarylene, and arylalkylene are each optionally interrupted with at least one of —O—, —C(O)—, —S(O)₀₋₂—, —N(R')—, —SO₂N(R')—, —C(O)N(R')—, —C(O)—O—, —O—C(O)—, —OC(O)N(R')—, —N(R')—C(O)—O—, or —N(R')—C(O)—N(R')—;

R' is hydrogen, alkyl having up to 4 carbon atoms, or —X—NR₂; and

R is hydrogen, alkyl, or hydroxalkyl.

In a ninth embodiment, the present disclosure provides a method according to the eighth embodiment, wherein X is alkylene.

In a tenth embodiment, the present disclosure provides a method according to any one of the first to ninth embodiments, wherein the fluorinated amine is represented by formula Rf—SO₂N(R')—X—NH₂, wherein Rf is perfluoroalkyl having up to 6 carbon atoms, R' is methyl, ethyl, or —X—NH₂, and X is alkylene having up to 4 carbon atoms.

In an eleventh embodiment, the present disclosure provides a method according to any one of the first to ninth embodiments, wherein the fluorinated amine is represented by formula Rf—C(O)—N(R')—X—NH₂, wherein Rf is perfluoropolyether having at least 10 fluorinated carbon atoms and at least three —O— groups, R' is methyl, ethyl, or —X—NH₂, and X is alkylene having up to 4 carbon atoms.

In a twelfth embodiment, the present disclosure provides a method according to any one of the first to fifth embodiments, wherein the fluorinated amine is polymeric.

In a thirteenth embodiment, the present disclosure provides a method according to the twelfth embodiment, wherein the polymeric fluorinated amine is represented by formula:

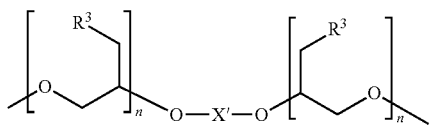

wherein each R³ is independently —X"—Rf or —NR₂,

Rf is fluoroalkyl having up to 10 carbon atoms, each X" is independently —N(R")SO₂—*, —N(R")CO—*, —O—C$_p$H$_{2p}$—*, —S—C$_p$H$_{2p}$—*, or —C$_q$H$_{2q}$—, with the * indicating the position to which the Rf is attached;

X' is alkylene that is optionally interrupted by one or more —O— groups;

R" is hydrogen or alkyl having 1 to 4 carbon atoms;

R is hydrogen, alkyl, or hydroxyalkyl;

p has a value from 0 to 6;

q has a value from 0 to 6; and each n is independently a value from 2 to 10 with the proviso that the polymeric fluorinated amine contains at least one —X"—Rf group and at least one —NR₂ group.

In a fourteenth embodiment, the present disclosure provides a method according to the twelfth embodiment, wherein the polymeric fluorinated amine is represented by formula:

first divalent units independently represented by formula:

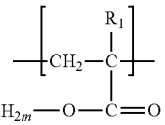

and second divalent units independently represented by formula:

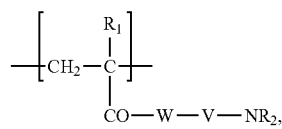

wherein

Rf is fluoroalkyl having from 1 to 10 carbon atoms;

each R¹ is independently hydrogen or methyl;

Q is a bond or —SO₂—N(R")—;

W is —O—, —S—, or —N(R")—;

each R" is independently hydrogen or alkyl having up to 4 carbon atoms;

V is alkylene that is optionally interrupted by at least one ether linkage or amine linkage and optionally substituted by hydroxyl;

each R is independently hydrogen, alkyl, or hydroxyalkyl; and m is an integer from 1 to 11.

In a fifteenth embodiment, the present disclosure provides a method according to any one of the first to fourteenth embodiments, further comprising treating the hydrocarbon-bearing formation with a fluid prior to contacting the surface of the hydrocarbon-bearing formation with the fluorinated amine, wherein the fluid comprises at least one of toluene, diesel, heptane, octane, condensate, water, methanol, ethanol, or isopropanol.

In a sixteenth embodiment, the present disclosure provides a method according to any one of the first to fifteenth embodiments, wherein the hydrocarbon-bearing formation is penetrated by a wellbore, and wherein a region near the wellbore is contacted with the composition.

In a seventeenth embodiment, the present disclosure provides a method according to any one of the first to sixteenth embodiments, further comprising fracturing the hydrocarbon-bearing formation, wherein contacting the surface of the hydrocarbon-bearing formation with a fluorinated amine is carried out during the fracturing, after the fracturing, or during and after the fracturing.

In an eighteenth embodiment, the present disclosure provides a method according to any one of the first to seventeenth embodiments, wherein the hydrocarbon-bearing formation has at least one fracture, and wherein the fracture has a plurality of proppants therein.

In a nineteenth embodiment, the present disclosure provides a method according to any one of the first to sixteenth embodiments, wherein the hydrocarbon-bearing formation is free of man-made fractures.

In a twentieth embodiment, the present disclosure provides a method according to any one of the first to nineteenth embodiments, wherein before contacting the hydrocarbon-bearing formation with the fluorinated amine, the hydrocarbon-bearing formation has at least one of brine or liquid hydrocarbons, and wherein the hydrocarbon-bearing formation has an increase in at least gas permeability after it is contacted with the fluorinated amine.

In a twenty-first embodiment, the present disclosure provides a hydrocarbon-bearing formation treated according to the method of any one of the first to twentieth embodiments.

In a twenty-second embodiment, the present disclosure provides a method of making a fluorinated amine, the method comprising:

combining a fluorinated compound having an acidic hydrogen and cyclic imidate represented by formula

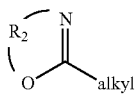

to provide a fluorinated amide; and hydroylzing the fluorinated amide to provide the fluorinated amine, wherein $R^2$ is a straight chain or branched alkylene having up to 10 carbon atoms, and wherein the $R^2$ group together with the —O—C(=N)— group form a five- or six-membered ring.

In a twenty-third embodiment, the present disclosure provides a method according to the twenty-second embodiment, wherein the fluorinated compound having an acidic hydrogen is represented by formula Rf'—SO$_2$N(R')—H or Rf'—CH$_2$OH, wherein the fluorinated amide is represented by formula Rf'—SO$_2$N(R')—R$^2$—N—C(O)-alkyl or Rf'—CH$_2$O—R$^2$—N—C(O)-alkyl, wherein the fluorinated amine is represented by formula Rf'—SO$_2$N(R')—R$^2$—NH$_2$ or Rf'—CH$_2$O—R$^2$—NH$_2$, wherein Rf' is fluoroalkyl having up to 10 carbon atoms, R$^2$ is a straight chain or branched alkylene having 2 or 3 in-chain carbon atoms and up to 10 carbon atoms total, and wherein R' is hydrogen, alkyl having up to 4 carbon atoms, or —R$^2$—NR$_2$.

In a twenty-fourth embodiment, the present disclosure provides a compound represented by formula Rf'—SO$_2$N(—R$^2$—NH$_2$)$_2$ or a salt thereof, wherein Rf' is fluoroalkyl having up to 10 carbon atoms; and each R$^2$ is independently a straight chain or branched alkylene having 2 or 3 in-chain carbon atoms and up to 10 carbon atoms total.

In a twenty-fifth embodiment, the present disclosure provides a polymeric fluorinated amine represented by formula:

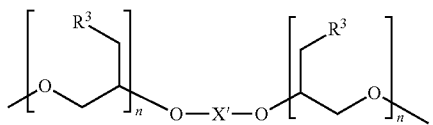

wherein each $R^3$ is independently —X"—Rf' or —NR$_2$,

Rf' is fluoroalkyl having up to 10 carbon atoms, each X" is independently —N(R")SO$_2$—*, —N(R")CO—*, —O—C$_p$H$_{2p}$—*, —S—C$_p$H$_{2p}$—*, or —C$_q$H$_{2q}$—, with the * indicating the position to which the Rf' is attached;

X' is alkylene that is optionally interrupted by one or more —O— groups;

R" is hydrogen or alkyl having 1 to 4 carbon atoms;

R is hydrogen, alkyl, or hydroxyalkyl;

p has a value from 0 to 6;

q has a value from 0 to 6; and each n is independently a value from 2 to 10 with the proviso that the polymeric fluorinated amine contains at least one —X"—Rf' group and at least one —NR$_2$ group.

Embodiments of the methods disclosed herein are further illustrated by the following examples, but the particular materials and amounts thereof recited in these examples, as well as other conditions and details, should not be construed to unduly limit this disclosure. Unless otherwise noted, all parts, percentages, ratios, etc. in the examples and the rest of the specification are by weight. In the Tables, "nd" means not determined.

EXAMPLES

The following compounds were obtained from VWR International, West Chester, Pa.: 2-butoxyethanol, ethanol, methane, n-butane, heptane, and decane.

N-methylperfluorobutanesulfonamide (MeFBSA) was prepared as described in Example 1 of U.S. Pat. No. 6,664,354 (Savu), incorporated herein by reference. Approximately 200 g of PBSF (perfluorobutanesulfonyl fluoride) distilled (est 95%, MW=302, 190 g active=0.63 mole) was charged to a 100 ml flask fitted with a −78° C. cold finger condenser, an overhead stirrer, thermocouple, and a plastic gas inlet tube. The flask was placed in a water bath, and with stirring addition of 43 g NH$_2$CH$_3$(MW=31, 1.38 moles) was started. After 10 minutes of gas addition, the temperature rose only 3° C. The internal temperature was raised by the addition of warm water to the bath to 50° C. and the gas addition rate was increased. The internal temperature was kept at 53-45° C. and the addition of NH$_2$CH$_3$ took approximately 40 minutes. The batch was allowed to stir at room temperature overnight. In the morning, the batch was heated to 50° C. with a heating mantle Approximately 300 ml water was added slowly to maintain the temperature. The batch was agitated for 15 minutes then allowed to split. The upper water layer was removed by vacuum decant (sucking off the top phase with the aspirator). This operation was repeated with an additional 300 ml of water. After washing twice with water, the batch was washed with 300 ml of a solution of 3% H$_2$S0$_4$, split and vacuum decanted. The acid washed fluorochemical (FC) bottom layer was washed three times with 300 ml of water, split and vacuum decanted each time. After the third wash the unused openings in the flask were stopped up, and a vacuum pump was attached to the flask. With stirring and at 45° C., the vacuum was slowly pulled on the flask to prevent spitting when residual water boils off too rapidly. The vacuum leveled off at 5 torr. The batch was heated to 60° C. at 5 torr vacuum for 30 min then at 85° C. for 15 min. The batch was cooled to 45° and vacuum was broken.

Preparation Example 1

N-(2-aminoethyl)-N-methylnonafluorobutanesulfonamide (C$_4$F$_9$SO$_2$NMeC$_2$H$_4$NH$_2$) was prepared according to the following description: 626 grams (2 moles) of MeFBSA, 198 grams of 2-ethyl-2-oxazoline (2 moles, commercially available from Avocado Research Chemicals, Lancashire, United Kingdom), and 17 grams of sodium carbonate (0.16 moles, commercially available from EM Science, Gibbstown, N.J.) were charged to a reactor and heated for 16 hours at 140° C. to form N-(2-(N-methylnonafluorobutanesulfonamido)ethyl)propionamide. The amide was twice extracted with 250 ml deionized water, heated for 18 hours at 100° C. with a mixture of 250 ml concentrated hydrochloric acid and 100 ml deionized water, extracted with 925 ml of 24 wt % aqueous sodium hydroxide solution, extracted with 250 ml 10 wt % aqueous sodium hydroxide solution, and distilled. Approximately 538 grams of N-(2-aminoethyl)-N-methylnonafluorobutanesulfonamide (75% recovery, 94% pure by GC) were distilled at 104-109° C. under 2 mm Hg pressure.

Preparation Example 2

N,N-Bis(aminoethyl)perfluorobutanesulfonamide was prepared by mixing 299 g (1 mol) of perfluorobutanesulfonamide ($C_4F_9SO_2NH_2$, prepared as described in U.S. Pat. No. 7,101,492 (Parent), column 9), and 17 g of $Na_2CO_3$. About 200 ml of bis(2-methoxyethyl)ether (diglyme, available from Sigma-Aldrich, St. Louis, Mo.) was heated to 130° C. and treated dropwise over 2 hours with 220 g (2.2 mol) of ethyl oxazoline (available from Aldrich Chemical, Milwaukee, Wis.). The mixture was heated for about 18 hours at 140-150° C., cooled to room temperature, and poured into 6 liters of water. Liquid chromatography coupled with mass-spectrometry (LC-MS) analysis showed the major component (67%) to be $C_4F_9SO_2N(C_2H_4NHCOC_2H_5)_2$, with lesser amounts of the mono-adduct $C_4F_9SO_2NHC_2H_4NHCOC_2H_5$ (8%) and the tri-adduct $C_4F_9SO_2N(C_2H_4NHCOC_2H_5)$—$C_2H_4N(COC_2H_5)$ $C_2H_4NHCOC_2H_5$ (12%). The resulting insoluble resin was mixed with 400 ml of 18% (v/v) HCl and stirred at reflux for 20 hours. On cooling, a solid precipitated. Addition of 500 ml of isopropanol and filtration yielded 246.6 g of an off-white solid and a second crop of 40.5 g. Both materials were shown by LC-MS to be the desired diadduct $C_4F_9SO_2N(C_2H_4NH_3Cl)_2$ with only traces of the mono- and triadducts. The materials were treated with 5 g of sodium methoxide (NaOMe) 25% in 20 ml of methanol. The solvent was subsequently stripped and the resulting solid was dissolved in 20 ml of tetrahydrofuran (THF). The solution was filtered and the THF stripped, yielding 4.1 g of oil.

Method Example 1

A treatment composition was prepared by mixing 346.1 g of 2-butoxyethanol, 145.08 g of ethanol and 10 g of $C_4F_9SO_2NMeC_2H_4NH_2$ (prepared as described above).

A core sample was cut from a block of limestone, (Texas cream limestone obtained from Texas Quarries, Round Rock, Tex.) having approximately a 7 millidarcy (mD) dry permeability.

Figure 2:
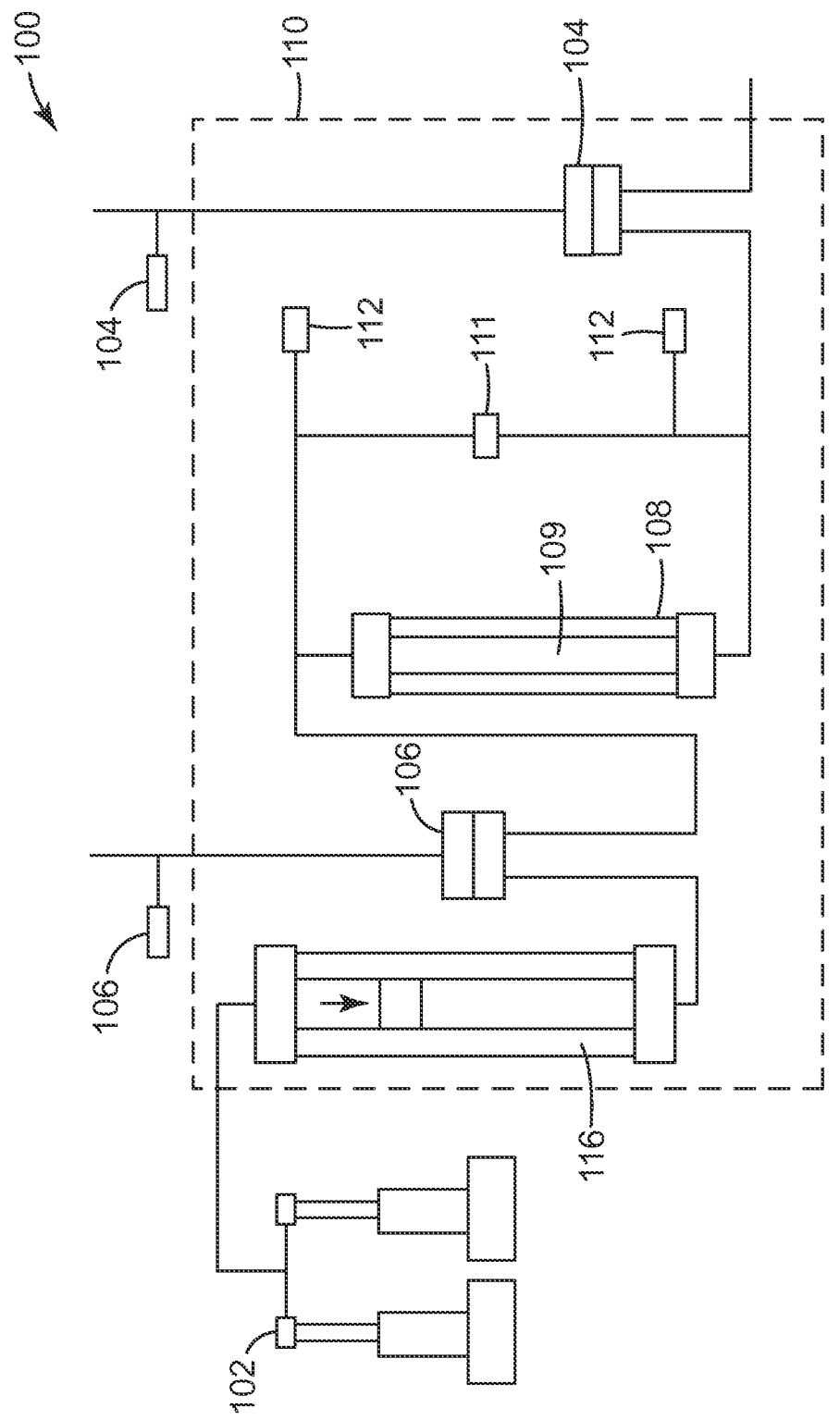
FIG. 2 is a schematic illustration of the core flood set-up used for Method Examples 1 and 2.

A schematic diagram of a core flood apparatus 100 used to determine relative permeability of a substrate sample (i.e., core) is shown in FIG. 2. Core flood apparatus 100 included positive displacement pump 102 (Model D-100; obtained from ISCO, Lincoln, Nebr.) to inject fluid at constant flow rates into fluid accumulator 116 (CFR series, obtained from Temco, Inc., Tulsa, Okla.). The pressure in the accumulator 116 was controlled and maintained by upstream backpressure regulator 106 (Model No. BPR-100 obtained from Temco, Inc.). Pressure ports 112 on high-pressure core holder 108 (Hassler-type Model RCHR-1.0 obtained from Tempo, Inc.) was used to measure pressure drop across the vertical core 109 by a differential pressure regulator 111 (Model 3051S obtained from Rosemount, Chanhassen, Minn.). The core pressure was regulated by a downstream back pressure regulator 104 (Model BPR-100 obtained from Tempo, Inc.). The pressures of back pressure regulators 104, 106 were measured at pressure ports P104, P106. The accumulator 116, the backpressure regulators 106, 104, and the coreholder 108 were all installed in an oven 110 (Model RFD2-19-2E obtained from Despatch, Lakeville, Minn.).

The core was dried for 72 hours in a standard laboratory oven at 95° C. and then wrapped in aluminum foil and heat shrink tubing. The wrapped core was then inserted into a fluorinated elastomer core sleeve and mounted onto the core holder. An overburden pressure of 1000 psi ($6.8 \times 10^6$ Pa) over the core pressure was applied in the core holder 108.

Fluid (e.g., nitrogen, gas condensate, or treatment composition) was delivered from accumulator 116 into the core 109. The absolute permeability of the core was measured with nitrogen at room temperature using at least four different flow rates to take the average. After the absolute permeability measurement, a brine composition comprising water and 3% KCl was introduced to the core by the following procedure to establish a saturation of 26% (i.e., 26% of the pore volume of the core was saturated with the brine). The outlet end of the core holder 108 was connected to a vacuum pump and a full vacuum was applied for 30 minutes with the inlet closed. The inlet was connected to a burette with the brine in it. The outlet was closed and the inlet was opened to allow the appropriate volume of brine to flow into the core. The inlet and outlet valves were then closed, and the brine was allowed to distribute in the core overnight.

A synthetic gas condensate made from 91.79 mole % methane, 3.94 mole % n-butane, 2.79 mole % heptane, and 1.47 mole % decane was prepared by weighing each component into accumulator 116. The gas condensate was then placed into the oven 110 on a pneumatically controlled rocker allowing it to reach equilibrium overnight at 275° F. (135° C.). The synthetic gas condensate was then injected into the core at a constant pump rate of 3.0 mL/minute. Upstream back-pressure regulator 106 was set at about 500 psi ($3.4 \times 106$ Pa) above the dew point pressure of the fluid, and downstream back-pressure regulator 104 was set at about 1500 psi ($3.38 \times 107$ Pa). The injection was continued until a steady state was reached. The gas relative permeability before treatment was then calculated from the steady state pressure drop. The treatment composition was then injected into the core. After at least about 20 pore volumes were injected, the treatment composition was held in the core at 145° F. (62.8° C.) for about 15 hours. The synthetic gas condensate fluid described above was then introduced again at the same rate using positive displacement pump 102 until a steady state was reached. The gas relative permeability after treatment was then calculated from the steady state pressure drop. The pressure drop (Δp) before treatment divided by the pressure drop (Δp) after treatment provides the improvement factor (PI).

Initial permeability of the core (Kabs), pressure change pre and post-treatment (Δp), capillary number pre and post-treatment (Nc) and the improvement factor (PI) were measured and are reported in Table 1, below.

TABLE 1

| Method Example | $K_{abs}$ (mD) | Pre-Treatment Δp (psi) | Pre-Treatment Nc | Post-Treatment Δp (psi) | Post-Treatment Nc | PI |
|---|---|---|---|---|---|---|
| 1 | 32.0 | 76.1 | $9.65 \cdot 10^{-5}$ | 37.3 | $4.69 \cdot 10^{-5}$ | 2.0 |

Method Example 2

The treatment composition was prepared and evaluated as described in Example 1, except that the fluorinated treatment composition was held in the core at 250° F. (121° C.).

Initial permeability of the core (Kabs), pressure change pre and post-treatment (Δp), capillary number pre and post-treatment (Nc) and the improvement factor (PI) were measured and are reported in Table 2, below.

TABLE 2

| Method Example | K$_{abs}$ (mD) | Pre-Treatment | | Post-Treatment | | PI |
|---|---|---|---|---|---|---|
| | | Δp (psi) | Nc | Δp (psi) | Nc | |
| 2 | 7.4 | 71.3 | $5.03 \cdot 10^{-5}$ | 46.5 | $3.28 \cdot 10^{-6}$ | 1.56 |

Method Example 3

A treatment composition using N,N-Bis(aminoethyl)perfluorobutanesulfonamide (prepared as described above) instead of $C_4F_9SO_2NMeC_2H_4NH_2$ can be evaluated according to the method of Example 1 to provide similar results.

Various modifications and alterations of this disclosure may be made by those skilled the art without departing from the scope and spirit of the disclosure, and it should be understood that this disclosure is not to be unduly limited to the illustrative embodiments set forth herein.

What is claimed is:

1. A method of modifying a surface of a hydrocarbon-bearing formation, the method comprising contacting the surface of the hydrocarbon-bearing formation with at least one of a fluorinated amine or an acid salt thereof, wherein the fluorinated amine is represented by formula Rf—SO$_2$N(R')—X—NH$_2$, wherein Rf is perfluoroalkyl having up to 6 carbon atoms, R' is methyl, ethyl, or —X—NH$_2$ and X is alkylene having us to 4 carbon atoms, and wherein the surface of the hydrocarbon-bearing formation comprises a carbonate.

2. A method according to claim 1, wherein contacting the surface of the hydrocarbon-bearing formation comprises introducing a treatment composition comprising solvent and the at least one of the fluorinated amine or the acid salt thereof into the hydrocarbon-bearing formation.

3. A method according to claim 2, wherein the treatment composition further comprises a fluorinated polymeric nonionic surfactant comprising a plurality of alkyleneoxy groups.

4. A method according to claim 2, wherein the solvent comprises at least one of water, a monohydroxy alcohol, an ether, a ketone, a glycol, a glycol ether, or supercritical carbon dioxide.

5. A method according to claim 1, wherein the hydrocarbon-beating formation is penetrated by a wellbore, and wherein a region near the wellbore is contacted with the treatment composition.

6. A method according to claim 1, wherein the hydrocarbon-bearing formation has at least one fracture, and wherein the fracture has a plurality of proppants therein.

7. A method according to claim 1, wherein the hydrocarbon-bearing formation is free of man-made fractures.

8. A hydrocarbon-bearing formation treated according to the method of claim 1.

9. A method according to claim 1, wherein the fluorinated amine is prepared by combining a fluorinated compound having an acidic hydrogen and cyclic imidate represented by formula

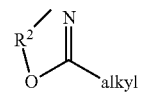

to provide a fluorinated amide; and
hydroylzing the fluorinated amide to provide the fluorinated amine,
wherein R$^2$ is a straight chain or branched alkylene having up to 4 carbon atoms, and wherein the R$^2$ group together with the —O—C(═N)— group form a five- or six-membered ring.

10. A method according to claim 1, wherein the fluorinated amine is represented by formula Rf"—SO$_2$N(—R$^2$—NH$_2$)$_2$, wherein
Rf" is perfluoroalkyl having up to 6 carbon atoms; and
each R$^2$ is independently a straight chain or branched alkylene having 2 or 3 in-chain carbon atoms and up to a total of 4 carbon atoms.

11. A method according to claim 1, further comprising treating the hydrocarbon-bearing formation with a fluid before contacting the surface of the hydrocarbon-bearing formation with the fluorinated amine, wherein the fluid comprises at least one of toluene, diesel, heptane, octane, condensate, water, methanol, ethanol, or isopropanol.

12. A method according to claim 1, wherein before contacting the hydrocarbon-bearing formation with the fluorinated amine, the hydrocarbon-bearing formation has at least one of brine or liquid hydrocarbons, and wherein the hydrocarbon-bearing formation has an increase in at least gas permeability after it is contacted with the fluorinated amine.

13. A method according to claim 1, further comprising fracturing the hydrocarbon-bearing formation, wherein contacting the surface of the hydrocarbon-bearing formation with a fluorinated amine is carried out during the fracturing, after the fracturing, or during and after the fracturing.

* * * * *